(12) United States Patent
Banerjee et al.

(10) Patent No.: US 12,347,572 B2
(45) Date of Patent: Jul. 1, 2025

(54) SYSTEM AND METHOD FOR MONITORING PATIENT HEALTH

(71) Applicants: Aniruddha Amal Banerjee, Vestal, NY (US); R. A. Ramanujan, Binghampton, NY (US)

(72) Inventors: Aniruddha Amal Banerjee, Vestal, NY (US); R. A. Ramanujan, Binghampton, NY (US)

( * ) Notice: Subject to any disclaimer, the term of this patent is extended or adjusted under 35 U.S.C. 154(b) by 0 days.

(21) Appl. No.: 18/400,600

(22) Filed: Dec. 29, 2023

(65) Prior Publication Data

US 2024/0136075 A1 Apr. 25, 2024

Related U.S. Application Data

(63) Continuation of application No. 16/902,982, filed on Jun. 16, 2020, now Pat. No. 11,862,347, which is a continuation-in-part of application No. 14/198,927, filed on Mar. 6, 2014, now Pat. No. 10,719,583.

(60) Provisional application No. 61/811,503, filed on Apr. 12, 2013.

(51) Int. Cl.
| | |
|---|---|
| G16H 80/00 | (2018.01) |
| G06F 21/62 | (2013.01) |
| G16H 10/60 | (2018.01) |
| G16H 20/10 | (2018.01) |
| G16H 20/60 | (2018.01) |
| G16H 20/70 | (2018.01) |
| G16H 30/20 | (2018.01) |
| G16H 40/67 | (2018.01) |

(52) U.S. Cl.
CPC ......... *G16H 80/00* (2018.01); *G06F 21/6245* (2013.01); *G16H 10/60* (2018.01); *G16H 20/10* (2018.01); *G16H 20/60* (2018.01); *G16H 20/70* (2018.01); *G16H 30/20* (2018.01); *G16H 40/67* (2018.01)

(58) Field of Classification Search
CPC ..... G16H 80/00; G16H 10/60; G06F 21/6245
See application file for complete search history.

(56) References Cited

U.S. PATENT DOCUMENTS

2011/0105854 A1* 5/2011 Kiani ............... G16Z 99/00
600/300

* cited by examiner

*Primary Examiner* — Evangeline Barr
(74) *Attorney, Agent, or Firm* — Heslin Rothenberg Farley & Mesiti P.C.

(57) ABSTRACT

A method, computer system, and computer program for improving communication between a patient and a provider are described. The method, computer system and computer program perform a method that includes: obtaining data related to the health state of a patient; associating a timestamp with the data, encrypting the data and writing the data to a computer readable medium, determining whether the data is in a pre-configured range, and responsive to determining that the data is not in the pre-configured range, sending an alert to a client. This method also includes obtaining a response from the client and writing the response to the computer readable medium, where the response includes a medical recommendation based on the data.

20 Claims, 37 Drawing Sheets

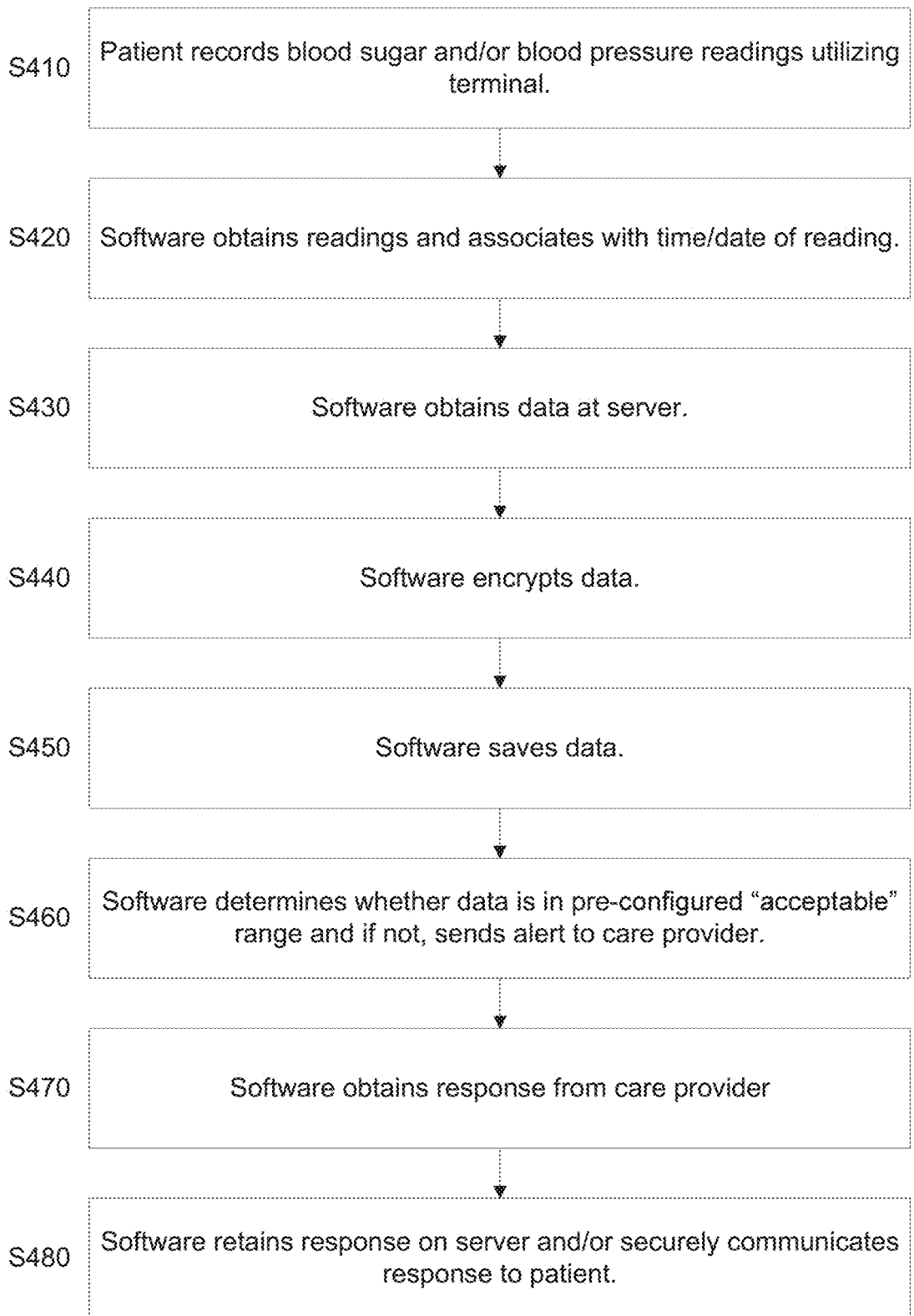

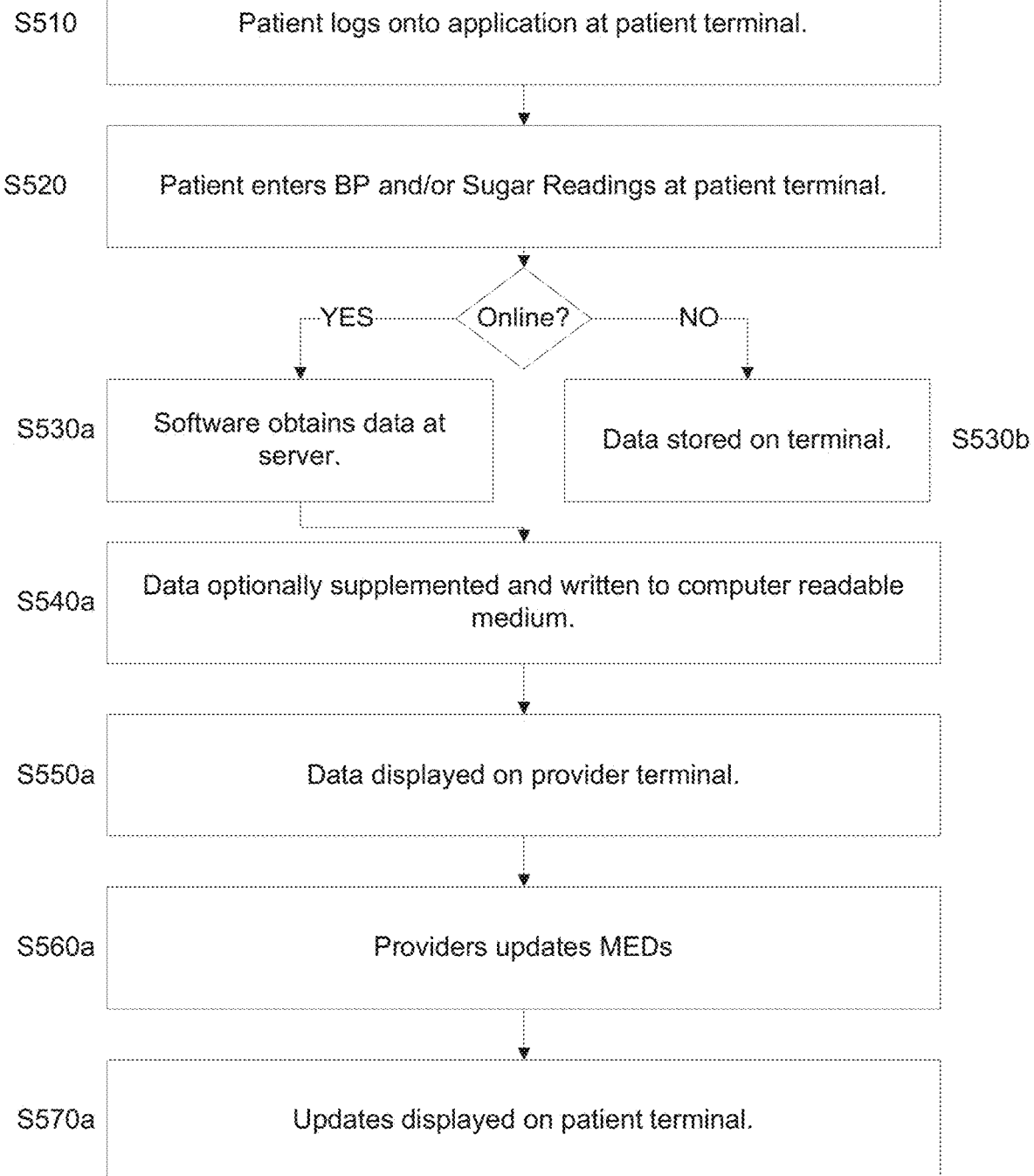

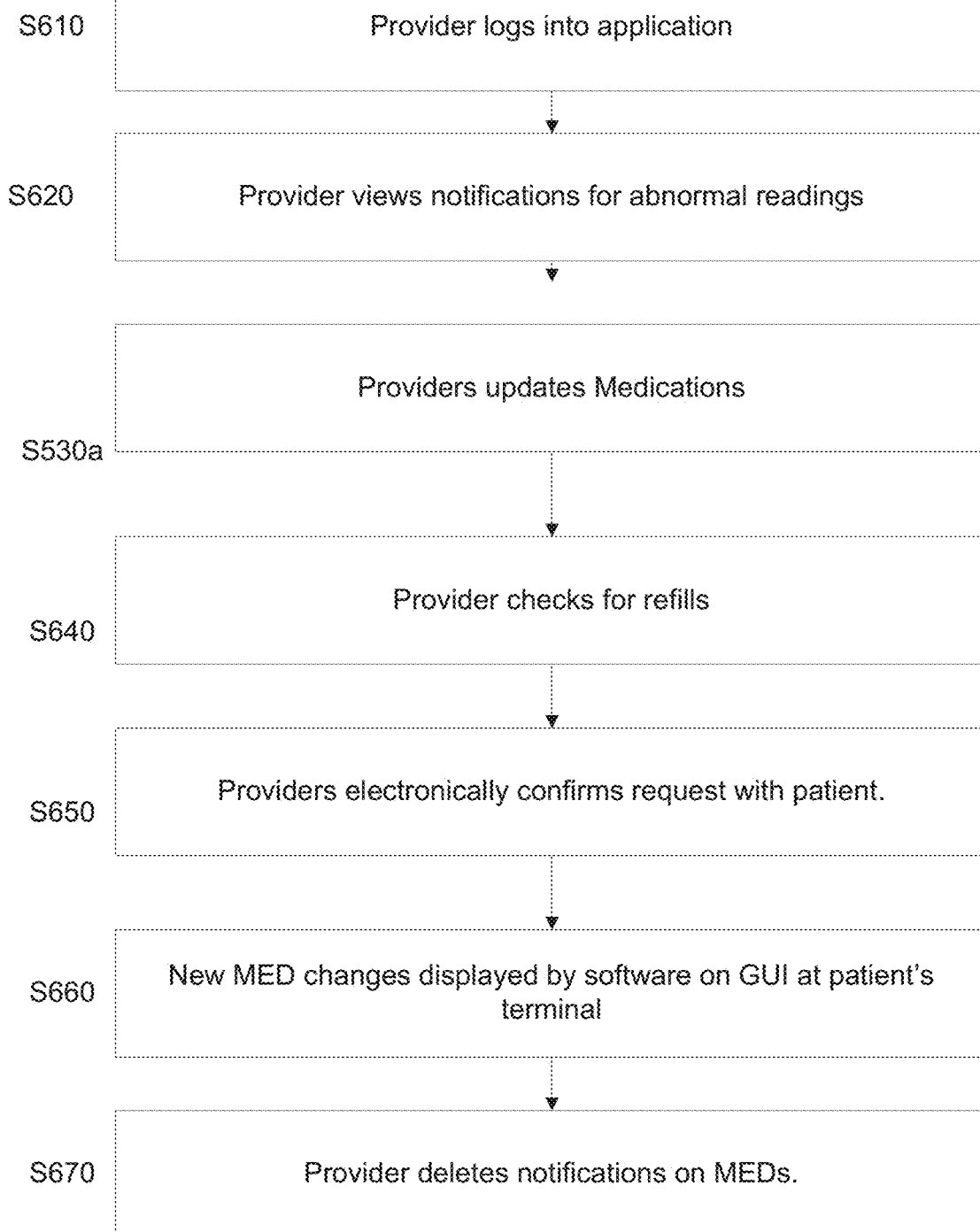

| Clinical Conditions | Drugs |
| --- | --- |
| Target Organ Damage | |
| Left Ventricular Hypertrophy | ARB |
| Microalbuminuria | ACEI, ARB |
| Asymptomatic atherosclerosis | CCB |
| Clinical Events | |
| History of Myocardial Infarction | BB, ACEI, ARB |
| Coronary Artery Disease | BB, ACEI, ARB, CCB (long acting) |
| Heart Failure | Thiazide diuretic, loop diuretic, BB, ACEI, ARB, MRA |
| Stroke | ACEI, ARB, Thiazide diuretic, CCB |
| Chronic Kidney Disease | ACEI, ARB, loop diuretic |
| Peripheral artery disease | CCB |
| Diabetes Mellitus | ACEI, ARB, DRI |
| Associated Conditions | |
| Isolated Systolic Hypertension | Thiazide diuretic, ACEI, ARB |
| Metabolic Syndrome | ACEI, ARB |

FIG 36

SYSTEM AND METHOD FOR MONITORING PATIENT HEALTH

CROSS REFERENCE TO RELATED APPLICATION

The present invention claims priority from U.S. patent application Ser. No. 16/902,982, filed Jun. 16, 2020, which claimed priority from U.S. patent application Ser. No. 14/198,927, filed Mar. 6, 2014, which claimed priority from U.S. provisional patent application No. 61/811,503, filed Apr. 12, 2013, each of which are hereby incorporated herein by reference in their entirety.

FIELD OF INVENTION

The Invention relates generally to systems and methods for enabling secure, real-time communication of health events and subsequent medical treatments between patients and care providers.

BACKGROUND

Medical conditions, such as, specifically, diabetes and hypertension, are health epidemics. In fact, today, over 25 million Americans have Type II Diabetes and 33% of the American population has been diagnosed with hypertension. These disease states can be controlled and/or reversed with the assistance of the continuous monitoring of the vital readings and diets of patients and the introduction of meal plans. Thus, individuals who suffer from these ailments require frequent attention from care providers, including regular visits to physicians, to manage the health state of the patients.

A number of factors can diminish the quality of care that a physician or other medical care provider is able to provide an individual suffering from hypertension and/or diabetes. These factors include: 1) office readings are not as accurate as home blood pressures readings; 2) patients don't typically keep track of their diets so a medical provider does not have this information when analyzing a patient's overall health and wellbeing; and 3) if a patient does monitor his or her health at home, the data collected through home monitoring systems, or on paper, does not became a part of the patient's medical record and cannot provide further insight and intelligence to the care provider. These factors all diminish a care giver's ability to accurately monitor a patient's vital readings and adherence to a meal plan.

SUMMARY

Shortcomings of the prior art are overcome and additional advantages are provided through the provision of a method for improving communication between a patient and a provider, the method includes: obtaining, by a processor, data related to the health state of a patient; associating, by the processor, a timestamp with the data, encrypting the data and writing the data to a computer readable medium; determining, by the processor, whether the data is in a pre-configured range; responsive to determining that the data is not in the pre-configured range, sending an alert to a client; and obtaining a response from the client and writing the response to the computer readable medium, where the response comprises a medical recommendation based on the data.

Shortcomings of the prior art are overcome and additional advantages are provided through the provision of a method for enabling streaming communications between a patient and a provider, the method includes: executing an interface on a remote care provider device, wherein the interface is configured to receive and to access data of patients associated with the care provider and to communicate with the patients; obtaining, at a secure HIPAA compliant server, from an interface on a mobile device over an Internet connection, data related to the health state of a patient selected from the patients, wherein the secure HIPAA compliant server comprises a processor and a computer readable medium that stores an electronic medical record comprising a medical record number of the patient, historical medical data for the patient associated with the medical record number, and contact information for the care provider for the patient, wherein the contact information is utilized to enable streaming communication between the patient and care provider; associating, by one or more processors of the secure HIPAA compliant server, a timestamp with the data, associating the data with the medical record number of the patient; writing, by the processor of the secure HIPAA compliant server, the data to the computer readable medium in an encrypted format; determining, by the one or more processors, whether the data is in a pre-configured range; determining, by the one or more processors, based on the contact information that the patient is associated with the care provider; responsive to determining that the data is not in the pre-configured range and that the patient is associated with the care provider, utilizing the contact information to transmit automatically a real-time alert in the encrypted format over a wireless communication channel to the remote care provider device, wherein, based on determining that the wireless device associated with the care provider is online, the alert is automatically displayed in the interface, and wherein based on determining that the wireless device associated with the care provider is not online, the alert is retained at a secured location and displayed in the interface when the wireless device associated with the care provider is online, wherein the displaying enables the care provider to utilize the interface to access, over the Internet, certain of the data related to the health of the patient and the historical medical data stored on the computer readable medium of the secure HIPAA compliant server, wherein the alert comprises personally identifiable patient data transmitted as an HL7 message file; responsive to the alert, obtaining a response from the wireless device associated with the care provider of the patient and associating the response with the medical record number of the patient and encrypting and writing the response to the computer readable medium in the encrypted format, wherein the response comprises a medical recommendation based on at least one of: the data, a portion of the historical medical data; and displaying, on the mobile device, instantaneously upon obtaining, the medical recommendation, based on the streaming communication.

Shortcomings of the prior art are overcome and additional advantages are provided through the provision of a method for enabling streaming communication between a patient and a provider, the method comprising: executing an interface on a remote care provider device, wherein the interface is configured to receive and to access data of patients associated with a care provider and to communicate the patients; obtaining, at a secure HIPAA compliant server, from a mobile device over an Internet connection, data related to the health state of a patient selected from the patients, wherein a first portion of the data is obtained upon submission, via an interface on the mobile device and a second portion of the data is obtained from a secured location on the mobile device, wherein the second portion of data was submitted through the interface when the mobile device was not connected to the secure HIPAA compliant server over the Internet and stored by the mobile device in the secured location of the mobile device, wherein the secure HIPAA compliant server comprises a processor and a computer readable medium that stores an electronic medical record comprising a medical record number of the patient, historical medical data for the patient associated with the medical record number, and contact information for the care provider for the patient, wherein the contact information is utilized to enable streaming communication between the patient and care provider; associating, by a processor of the secure HIPAA compliant server, a timestamp with the data, associating the data with the medical record number of the patient; writing, by the processor of the secure HIPAA compliant server, the data to the computer readable medium in an encrypted format, wherein the writing comprises: encrypting the data; converting the data to a first set of HL7 embedded portable document format (PDF) message files; and writing the first set of HL7 embedded portable document format (PDF) message files into the electronic medical record; determining, by the processor, whether the data is in a pre-configured range; determining, by the processor, based on the contact information that the patient is associated with the care provider; responsive to determining that the data is not in the pre-configured range and that the patient is associated with the care provider, utilizing the contact information to transmit automatically a real-time alert in the encrypted format over a wireless communication channel to the remote care provider device, wherein the alert is automatically displayed in the interface, wherein the displaying enables the care provider to utilize the interface to access, over the Internet, certain of the data related to the health of the patient and the historical medical data stored on the computer readable medium of the secure HIPAA compliant server, wherein the alert comprises personally identifiable patient data transmitted as an HL7 message file; responsive to the alert, obtaining a response from the wireless device associated with the care provider of the patient and associating the response with the medical record number of the patient and encrypting and writing the response to the computer readable medium in the encrypted format, wherein the response comprises a medical recommendation based on at least one of: the data, a portion of the historical medical data; displaying, on the mobile device, instantaneously upon obtaining, the medical recommendation, based on the streaming communication, wherein the medical recommendation comprises a diet plan; based on obtaining the diet plan, executing a query on a memory resource selected from the group consisting of an external memory resource and an internal memory resource; responsive to the query, obtaining information describing one or more products compatible with the diet plan; and displaying the information on the mobile device.

Shortcomings of the prior art are overcome and additional advantages are provided through the provision of a method for enabling streaming communication between a patient and a provider, the method comprising: executing an interface on a remote care provider device, wherein the interface is configured to receive and to access data of patients associated with the care provider and to communicate the patients; obtaining, at a secure HIPAA compliant server, from an interface on a mobile device over an Internet connection, data related to the health state of a patient selected from the patients, wherein the secure HIPAA compliant server comprises a processor and a computer readable medium that stores an electronic medical record comprising a medical record number of the patient, historical medical data for the patient associated with the medical record number, and contact information for the care provider for the patient, wherein the contact information is utilized to enable streaming communication between the patient and care provider; associating, by a processor of the secure HIPAA compliant server, a timestamp with the data, associating the data with the medical record number of the patient; writing, by the processor of the secure HIPAA compliant server, the data to the computer readable medium in an encrypted format, wherein the writing comprises: encrypting the data; converting the data to a first set of HL7 embedded portable document format (PDF) message files; and writing the first set of HL7 embedded portable document format (PDF) message files into the electronic medical record; determining, by the processor, whether the data is in a pre-configured range; determining, by the processor, based on the contact information that the patient is associated with the care provider; responsive to determining that the data is not in the pre-configured range and that the patient is associated with the care provider, utilizing the contact information to transmit automatically a real-time alert in the encrypted format over a wireless communication channel to the remote care provider device, wherein, based on determining that the wireless device associated with the care provider is online, the alert is automatically displayed in the interface, and wherein based on determining that the wireless device associated with the care provider is not online, the alert is retained at a secured location and displayed in the interface when the wireless device associated with the care provider is online, wherein the displaying enables the care provider to utilize the interface to access, over the Internet, certain of the data related to the health of the patient and the historical medical data stored on the computer readable medium of the secure HIPAA compliant server, wherein the alert comprises personally identifiable patient data transmitted as an HL7 message file; responsive to the alert, obtaining a response from the wireless device associated with the care provider of the patient and associating the response with the medical record number of the patient and encrypting and writing the response to the computer readable medium in the encrypted format, wherein the response comprises a medical recommendation based on at least one of: the data, a portion of the historical medical data; displaying, on the mobile device, instantaneously upon obtaining, the medical recommendation, based on the streaming communication, wherein the medical recommendation comprises a diet plan; based on obtaining the diet plan, executing a query on a memory resource selected from the group consisting of an external memory resource and an internal memory resource; responsive to the query, obtaining information describing one or more products compatible with the diet plan; and displaying the information on the mobile device.

Computer systems, computer program products and methods relating to one or more aspects of the technique are also described and may be claimed herein. Further, services relating to one or more aspects of the technique are also described and may be claimed herein.

Additional features are realized through the techniques of the present invention. Other embodiments and aspects of the invention are described in detail herein and are considered a part of the claimed invention.

BRIEF DESCRIPTION OF DRAWINGS

The foregoing and objects, features, and advantages of one or more aspects of the invention are apparent from the following detailed description taken in conjunction with the accompanying drawings in which:

FIGS. 4, 4A, and 4B depict aspects of a dataflow model of an embodiment of the present invention;

FIGS. 26-34 depict various aspects of user interfaces and functionalities comprising these interfaces, as generated by program code in some embodiments of the present invention;

FIGS. 36-37 are illustrations of various resources or references available to a care provider utilizing aspects of some embodiments of the present invention when utilizing an interface generated by the program code in embodiments of the present invention.

DETAILED DESCRIPTION OF THE INVENTION

Figure 1:
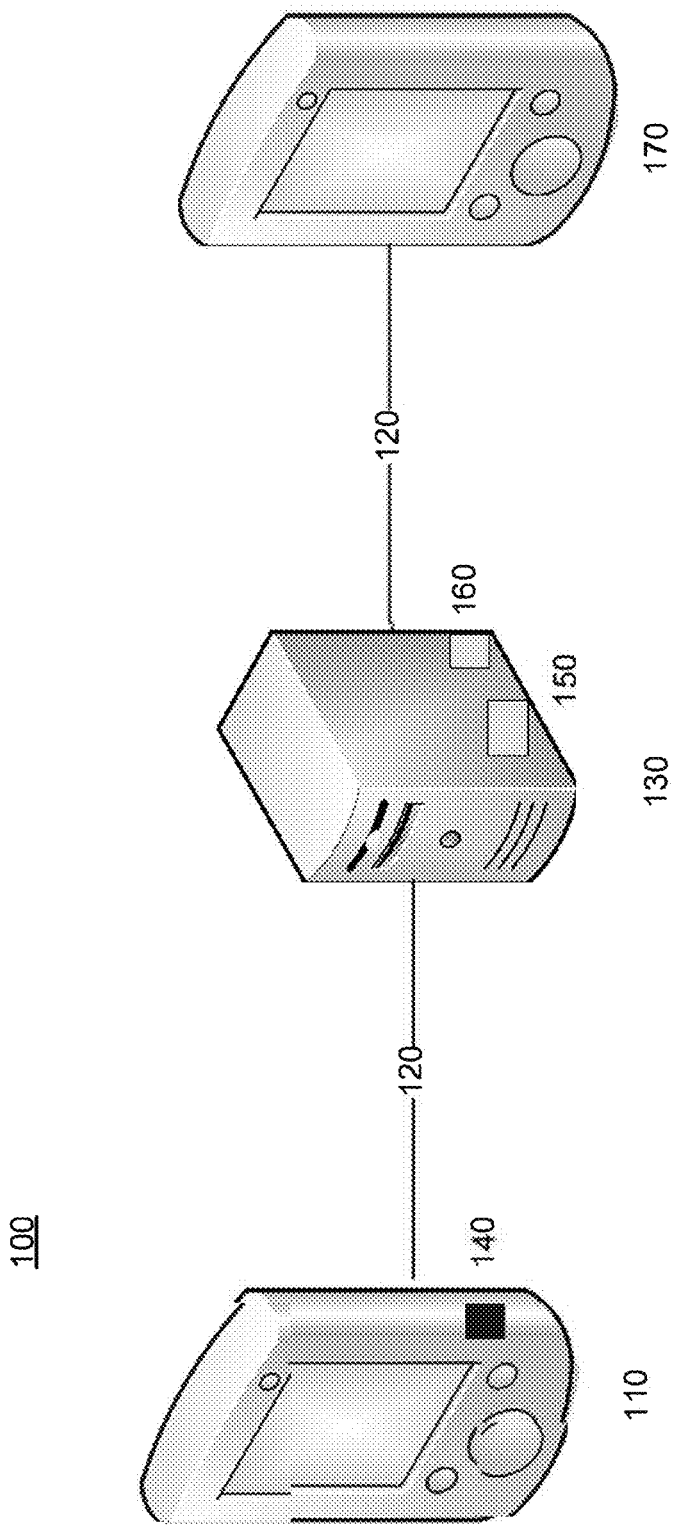
FIG. 1 depicts one example of an aspect a computing environment used to execute one or more aspects of an embodiment of the present invention.

Aspects of the present invention and certain features, advantages, and details thereof, are explained more fully below with reference to the non-limiting examples illustrated in the accompanying drawings. Descriptions of well-known materials, fabrication tools, processing techniques, etc., are omitted so as not to unnecessarily obscure the invention in detail. It should be understood, however, that the detailed description and the specific examples, while indicating aspects of the invention, are given by way of illustration only, and not by way of limitation. Various substitutions, modifications, additions, and/or arrangements, within the spirit and/or scope of the underlying inventive concepts will be apparent to those skilled in the art from this disclosure. The terms software and program code are used interchangeably throughout this application and can refer to logic executed by both hardware and software. Components of the system that can be utilized to execute aspects of embodiments of the present invention may include specialized hardware, including but not limited to, a GPP, an FPGA and a GPU (graphics professor unit). Additionally, items denoted as processors may include hardware and/or software processors or other processing means, including but not limited to a software defined radio and/or custom hardware.

Embodiments of the present invention include a computer-implemented method, a computer program product, and a computer system, which include program code executing on at least one server that enables patients seeking medical treatment for conditions that benefit from regular monitoring, such as hypertension and/or diabetes, to communicate their blood sugar and other vital readings to physicians, in a secure manner, in real-time, and receive medical treatment (including recommendations for treatment) quickly (e.g., in real-time and/or in near real time) over this secure connection. Embodiments of the present invention additionally include a computer system and method that enables physicians and/or other health care providers to utilize a communications connection with a patient to diagnose issues and provide treatment (and recommendations for treatment).

Aspects of embodiments of the present invention provide a global, scalable solution, which is usable and compatible across computing and communications platforms. By utilizing aspects of the present technique, a patient can take various health-related readings and communicates these readings, in a greater context supplied by the technique, to a specific physician through a live stream, allowing the physician to react to the readings and communicate adjustments to the patient, based on this information. This live stream offers improved disease management, and the patient gets "better than office visit" outcomes. This technique offers the physician a more effective way to monitor patients with, for example, diabetes and high blood pressure. By utilizing aspects of the technique, the patient is monitored closely without having to leave home/work/school for physician appointments.

By utilizing and embodiment of the present invention, patients monitor disease states in the comfort of their homes/offices/schools, and this embodiment can communicate the readings safely, for example, utilizing encryption, to care providers, in real time, for interpretation and treatment. As explained herein, in embodiments of the present invention, a combination of one or more of passive and/or active monitoring techniques can be utilized.

In an aspect of the present invention, embodiments of the system and method provide secure, HIPAA compliant storage of patient-specific readings.

In an aspect of the present invention, embodiments of the system and method enable secure real-time communications between the patient and physician.

In an aspect of the present invention, embodiments of the system and method enable the integration of data recorded by patients, such as blood pressure readings and dietary choices, into a patient's electronic medical record.

Aspects of various embodiments of the present invention are inextricably linked to computing. For example, certain aspects of some embodiments of the present invention are directed to utilizing features inextricably linked to computing in an improved user interface. In some embodiments of the present invention, the user interfaces generated by the program code (executing on one or more processors) provide data to care providers and patients in real-time, in a novel manner. Additionally, aspects of various embodiments of the present invention also provide a practical application, through the use of computing technology. Aspects of embodiments of the present invention provide time-sensitive data to individuals with an immediacy while also complying with specific data security protocols. Regarding the security aspects, in some embodiments of the present invention, program code executing on a secure HIPAA compliant server writes data in an encrypted format, encrypting the data, converting the data to HL7 embedded portable document format (PDF) message files, and writing the HL7 embedded portable document format (PDF) message files into the electronic medical record. As an example of temporal aspects of some embodiments of the present invention that provide practicality because computing technology enables these time-sensitive aspects are various types of alerts to certain users. For example, in some embodiments of the present invention, when program code executing on one or more processors determines that data is not in a pre-configured range for a given patient and that given patient is associated with a given care provider, the program code utilizes contact information stored within the system to transmit automatically a real-time alert in an encrypted format, over a wireless communication channel to the care provider, who is located remotely. This alert is populated by the program code on a provider's computing device. The program code determines that the provider's computing device, a wireless device is online and is associated with the care provider and automatically displays the alert in an interface the program code generates on the device. But the program code can also determine that the device is not online, and, in this event, the program code can retain the alert at a secured location and display in the interface when the wireless device associated with the care provider is online. Displaying enables the care provider to utilize the interface to access, over the Internet, certain of the data related to the health of the patient and the historical medical data stored on the computer readable medium of a secure HIPAA compliant server, which is part of the system disclosed herein. The alert can comprise personally identifiable patient data transmitted as an HL7 message file. An additional aspect of some embodiments of the present invention that relates to security is that in some embodiments of the present invention program code executing on a secure HIPAA compliant server (which is part of a system disclosed herein), obtains from a mobile device, over an Internet connection, data related to the health state of a patient. The data obtained by the program code includes both data obtained upon submission (i.e., via the interface on the mobile device) and data obtained from a secured location on the mobile device. The data from the secured location was submitted through the interface when the mobile device was not connected to the secure HIPAA compliant server over the Internet and stored by the mobile device in the secured location of the mobile device.

Embodiments of the present invention provide significant advantages over existing approaches for electronic communication between a patient and a provider. Listed in this paragraph are just some of the advantages and are not meant to suggest any limitations. As discussed herein, the communications provided by various embodiments of the present invention are streaming communications, which provides for more timely healthcare because delays are eliminated (while maintaining information security through various protections described herein). In addition to providing this streaming communications, in embodiments of the present invention, program code executed by the processor of the secure HIPAA compliant server writes data (which can include data entered by a user and the aforementioned secured data) to a computer readable medium in an encrypted format. This writing can include encrypting the data, converting the data to a first set of HL7 embedded portable document format (PDF) message files, and writing the first set of HL7 embedded portable document format (PDF) message files into an electronic medical record. Another advantage over existing patient-caregiver communication systems is that in some embodiments of the present invention, the program code sends alerts that include personally identifiable patient data transmitted as an HL7 message file. Another non-limiting example of advantages over existing patient-caregiver communication systems is that in embodiments of the present invention program code executed by a processor displays, on a mobile device, instantaneously upon obtaining, a medical recommendation, based on the streaming communication. This recommendation can include a diet plan. Based on obtaining the diet plan, the program code can execute a query on a memory resource selected from the group consisting of an external memory resource and an internal memory resource and in response to the query, the program code can obtain information describing one or more products compatible with the diet plan and display this information on the mobile device.

As discussed in reference to FIG. 1, below, in an aspect of the present invention, embodiments of the system and method are accessible via a variety of computing terminals, including but not limited to, smartphones, tablets, laptops and/or desktops.

In an aspect of the present invention, embodiments of the system and method enable ease of implementation of ay disaster recovery solution, including the use of a hot or cold backup, including a dedicated backup server to the server 130 in FIG. 1, by centralizing data obtained and utilized by the invention, as seen in the technical architecture of FIG. 1.

In an aspect of the present invention, embodiments of the system and method enable rapid notification of a physician or other medical care provider when a patient exhibits vital signs and/or readings outside of an acceptable range. Due to this rapid notification, the physician and/or care provider can react to the information, including prescribing a drug treatment, or a course of treatment including exercise, diet, etc.

In an aspect of the present invention, embodiments of the system and method enable the monitoring and adjustment of the dietary habits of a patient as the real-time communication between a patient and a care giver, such as a nutritionist or dietician, provides can provide and monitor a meal plan pertaining to a patient.

FIG. 1 is a computing environment 100 used to execute one or more aspects of an embodiment of the present invention. Terminal 110 is a user terminal that includes, but is not limited to, a mobile device. A mobile device is a particularly effective terminal 110 as it enables a user to communicate health states from unlimited locations. Terminal 110 can include, but is not limited to, a laptop, a desktop, a smartphone, and a tablet. For ease of understanding, only a single terminal 110 is shown in FIG. 1, but the system architecture is scalable to communicate with and obtain data from numerous terminals. One of the skills in the art will recognize that it is advantageous to utilize a mobile device as terminal 110, however, this example is not limiting.

In the embodiment of FIG. 1, terminal 110 communicates over a wireless computing network 120 with a secure, encrypted, Health Insurance Portability and Accountability Act (HIPAA) compliant server 130. In a further embodiment of the present invention, software 140 (computer code executed by a processor) on the terminal 110, encrypts information sent over the network 120 to the server 130. In a further embodiment of the present invention, the wireless network 120 is not a public network, such that only certain terminals, such as terminal 110 can communicate over the network 120 with the server 130. For example, the when the network 120 is private, it can include, but is not limited to, a virtual private network (VPN) and/or a privately leased line. One skill in the art will recognize that the connection between the terminal 110 and the server 130 can be privatized in various ways known in the art in order to limit communications to the server 130 to one or more of a select group of terminals. In a further embodiment of the present invention, software 160 executed at the server 130 encrypts the communications from the terminal 110 to the server 130.

In an embodiment of the present invention, the server 130 includes a computer readable storage medium 150, such as a database, including but not limited to a SQL Server, which stores historical data related to users of the system, including such data related to the user of terminal 110. When the server 130 receives data from a terminal 110 via the network 120, software 160 executed by a processor on the server 130 can store the data in the computer readable storage medium 150, compare the data to data stored in the computer readable storage medium 150, and/or retrieve related data from the computer readable storage medium 150. Software 160 executed by one or more processors of the server 130 sends the data from the terminal 110, and in embodiments of the present invention, additional data retrieved from the computer readable medium 150, over a secure network connection to a care provider terminal 170, which is a mobile terminal in embodiments of the present invention. In further embodiments of the present invention, the software 160 will display the data from the terminal and/or data retrieved from a computer readable storage medium 150 on a GUI (not pictured) viewable on the care provider terminal 170.

The system and method comply with HIPAA guidelines for securing patient information. To this end, in embodiments of the present invention, the software 160 obtains data and encrypts the data before saving it in the computer readable storage medium 150.

In further embodiments of the present invention, the software 160 will send a notification to the care provider terminal 170, notifications include, but are not limited to, emails, text messages, and/or voice messages, and enable the user of the care provider terminal 170 to access the data obtained by the server 130 from the terminal 110 and/or the historical data maintained by the software 160 in the computer readable storage medium 150. In a further embodiment of the present invention, the software 160 will determine whether the data obtained from the terminal 110 is outside pre-configured "acceptable" parameters, and send an alert to a care provider, via a communications connection with the care provider terminal 120 when the software 160 determines that the readings are not within the acceptable range.

In further embodiments of the present invention, the on the server 130 will create an HL7 message file, standard message that is compliant with the standards created by Health Level Seven to comply with HIPAA's privacy guidelines.

Although FIG. 1 describes computer readable storage medium 150 as being a component of the server 130, further embodiments of the present invention utilize one or more computer readable media that are internal and/or external to the physical server but are accessible to the software 160 executed by the one or more processors of the server 130.

In the embodiment of FIG. 1, server 130 is a web server and, therefore, the terminal 110 and the care provider terminal 170 utilize thin clients, such as browsers, to access the software 160, that is executed on the server 130. Varying embodiments of the present invention may utilize a fat client version and may install components of the software 160 on the terminal 100, the server 130, and/or the care provider terminal 170.

Figure 2:
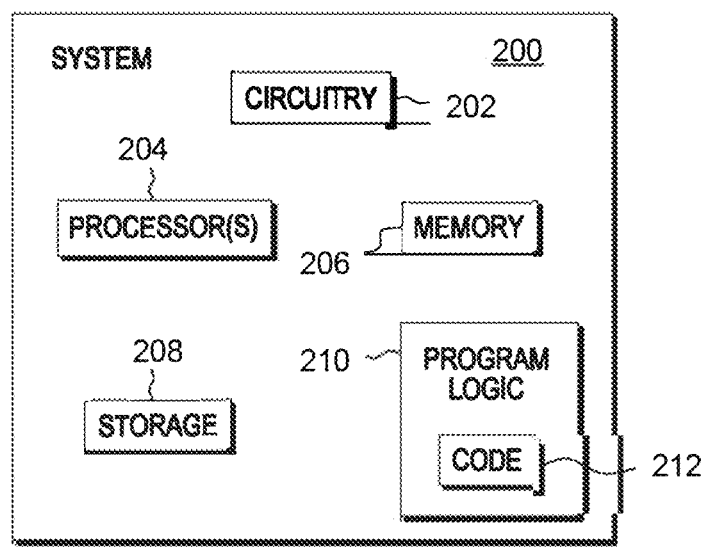
FIG. 2 depicts one embodiment of a single processor computing environment to incorporate and use one or more aspects of the present invention.

FIG. 2 illustrates a block diagram of a resource 200, like terminal 110 and/or server 130, and/or care giver terminal 170 in computer system 100, which is part of the technical architecture of certain embodiments of the technique. The resource 200 may include a circuitry 202 that may in certain embodiments include a microprocessor 204. The computer system 200 may also include a memory 206 (e.g., a volatile memory device), and storage 208. The storage 208 may include a non-volatile memory device (e.g., EEPROM, ROM, PROM, RAM, DRAM, SRAM, flash, firmware, programmable logic, etc.), magnetic disk drive, optical disk drive, tape drive, etc. The storage 208 may comprise an internal storage device, an attached storage device and/or a network accessible storage device. The system 200 may include a program logic 210 including code 212 that may be loaded into the memory 206 and executed by the microprocessor 204 or circuitry 202.

In certain embodiments, the program logic 210 including code 212 may be stored in the storage 208, or memory 206. In certain other embodiments, the program logic 210 may be implemented in the circuitry 202. Therefore, while FIG. 2 shows the program logic 210 separately from the other elements, the program logic 210 may be implemented in the memory 206 and/or the circuitry 202.

Using the processing resources of a resource 200 to execute software, computer-readable code or instructions, does not limit where this code can be stored. The terms program logic, code, and software are used interchangeably throughout this application.

Figure 3:
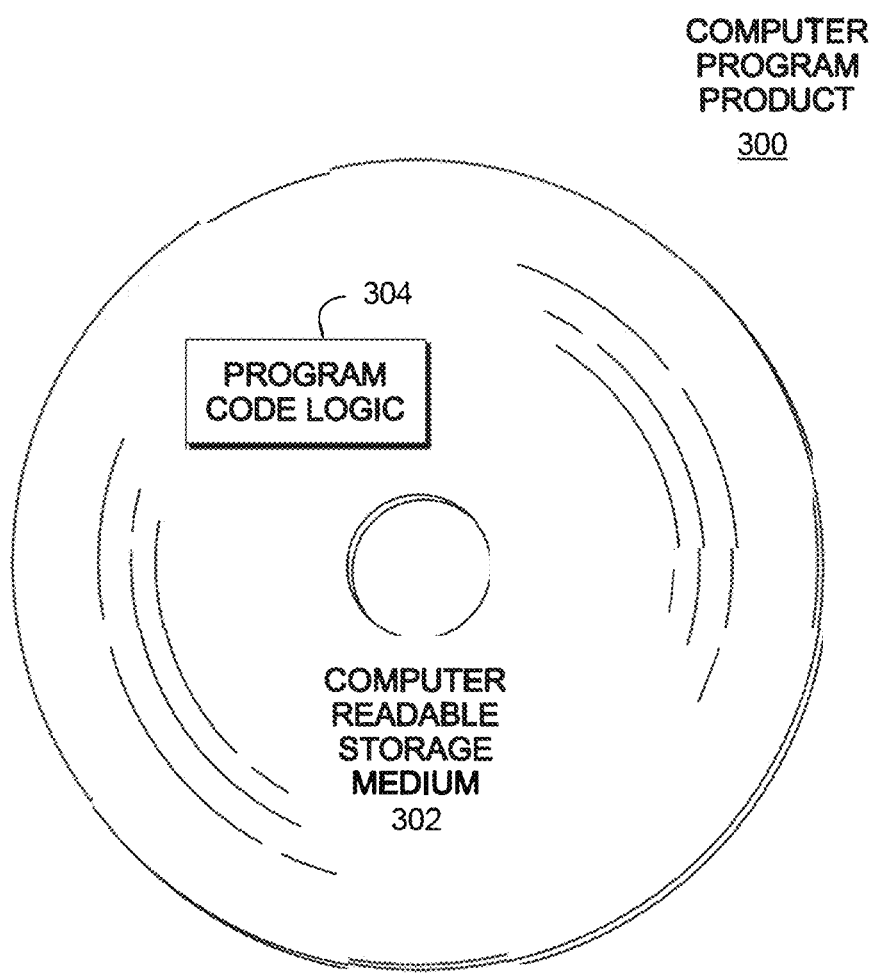
FIG. 3 depicts one embodiment of a computer program product incorporating one or more aspects of the present invention.

Referring to FIG. 3, in one example, a computer program product 300 includes, for instance, one or more non-transitory computer readable storage media 302 to store computer readable program code means or logic 304 thereon to provide and facilitate one or more aspects of the technique.

As will be appreciated by one skilled in the art, aspects of the technique may be embodied as a system, method or computer program product. Accordingly, aspects of the technique may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the technique may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable signal medium may include a propagated data signal with computer readable program code embodied therein, for example, in baseband or as part of a carrier wave. Such a propagated signal may take any of a variety of forms, including, but not limited to, electro-magnetic, optical or any suitable combination thereof. A computer readable signal medium may be any computer readable medium that is not a computer readable storage medium and that can communicate, propagate, or transport a program for use by or in connection with an instruction execution system, apparatus or device.

A computer readable storage medium may be, for example, but not limited to, an electronic, magnetic, optical, electromagnetic, infrared or semiconductor system, apparatus, or device, or any suitable combination of the foregoing. More specific examples (a non-exhaustive list) of the computer readable storage medium include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device.

Program code embodied on a computer readable medium may be transmitted using an appropriate medium, including but not limited to wireless, wireline, optical fiber cable, RF, etc., or any suitable combination of the foregoing.

Computer program code for carrying out operations for aspects of the technique may be written in any combination of one or more programming languages, including an object oriented programming language, such as Java, Smalltalk, C++ or the like, and conventional procedural programming languages, such as the "C" programming language, assembler or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the technique are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions, also referred to as computer program code, may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the figures illustrate the architecture, functionality, and operation of possible implementations of systems, methods and computer program products according to various embodiments of the technique. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

In addition to the above, one or more aspects of the technique may be provided, offered, deployed, managed, serviced, etc. by a service provider who offers management of customer environments. For instance, the service provider can create, maintain, support, etc. computer code and/or a computer infrastructure that performs one or more aspects of the technique for one or more customers. In return, the service provider may receive payment from the customer under a subscription and/or fee agreement, as examples. Additionally, or alternatively, the service provider may receive payment from the sale of advertising content to one or more third parties.

In one aspect of the technique, an application may be deployed for performing one or more aspects of the technique. As one example, the deploying of an application comprises providing computer infrastructure operable to perform one or more aspects of the technique.

As a further aspect of the technique, a computing infrastructure may be deployed comprising integrating computer readable code into a computing system, in which the code in combination with the computing system is capable of performing one or more aspects of the technique. As a further aspect of the technique, the system can operate in a peer to peer mode where certain system resources, including but not limited to, one or more databases, is/are shared, but the program code executable by one or more processors is loaded locally on each computer (workstation).

As yet a further aspect of the technique, a process for integrating computing infrastructure comprising integrating computer readable code into a computer system may be provided. The computer system comprises a computer readable medium, in which the computer medium comprises one or more aspects of the technique. The code in combination with the computer system is capable of performing one or more aspects of the technique.

Further, other types of computing environments can benefit from one or more aspects of the technique. As an example, an environment may include an emulator (e.g., software or other emulation mechanisms), in which a particular architecture (including, for instance, instruction execution, architected functions, such as address translation, and architected registers) or a subset thereof is emulated (e.g., on a native computer system having a processor and memory). In such an environment, one or more emulation functions of the emulator can implement one or more aspects of the technique, even though a computer executing the emulator may have a different architecture than the capabilities being emulated. As one example, in emulation mode, the specific instruction or operation being emulated is decoded, and an appropriate emulation function is built to implement the individual instruction or operation.

In an emulation environment, a host computer includes, for instance, a memory to store instructions and data; an instruction fetch unit to fetch instructions from memory and to optionally, provide local buffering for the fetched instruction; an instruction decode unit to receive the fetched instructions and to determine the type of instructions that have been fetched; and an instruction execution unit to execute the instructions. Execution may include loading data into a register from memory; storing data back to memory from a register; or performing some type of arithmetic or logical operation, as determined by the decode unit. In one example, each unit is implemented in software. For instance, the operations being performed by the units are implemented as one or more subroutines within emulator software.

Further, a data processing system suitable for storing and/or executing program code is usable that includes at least one processor coupled directly or indirectly to memory elements through a system bus. The memory elements include, for instance, local memory employed during actual execution of the program code, bulk storage, and cache memory which provide temporary storage of at least some program code in order to reduce the number of times code must be retrieved from bulk storage during execution.

Input/Output or I/O devices (including, but not limited to, keyboards, displays, pointing devices, DASD, tape, CDs, DVDs, thumb drives and other memory media, etc.) can be coupled to the system either directly or through intervening I/O controllers. Network adapters may also be coupled to the system to enable the data processing system to become coupled to other data processing systems or remote printers or storage devices through intervening private or public networks. Modems, cable modems, and Ethernet cards are just a few of the available types of network adapters.

As will be understood by those of skill in the art, privacy and security are important components of any system that transmits medical data. The present invention provides a number of advantages to ensure privacy and security are preserved and health care privacy guidelines are complied with. Embodiments of the present are configured so that a physician and/or care provider can only utilize the system and method to communicate with his or her own patients exclusively and receive and review data from his or her own patients, exclusively. Another advantage is that patients can securely utilize the system and method to send multiple readings regarding their health states to their care providers, which ensures a more accurate diagnosis and/or recommendation, by the recipient of the information. In embodiments of the present invention, these multiple readings are date/time stamped and sent to a physician or care provider via a secure, encrypted, HIPAA compliant server 130. Thus, the server 130 is easily integrated into the patient electronic medical record and eliminates office visits for the patient. Embodiments of the present invention provide an advantage by enabling streaming communication between the patient and physician, while integrating blood pressure, blood sugar, pulse and diet, for a complete picture of the patient.

FIG. 4 is a workflow 400 of one or more aspects of an embodiment of the present invention. When referring to FIG. 4, components of the technical environment of FIG. 1 are referenced for ease of understanding, however, one of skill in the art will recognize that aspects of the present invention can be implementing across a variety of technical environments.

A patient utilizes the terminal 110 to record his or her own blood sugar and/or blood pressure readings (S410). The user can manually enter this information and/or a device that provides these reading can be communicatively attached to the terminal 110 so that the terminal can receive these readings. The software 160 obtains the readings, associates the readings with the time in which they were provided, for example, by adding a date/time stamp (S420) and, optionally, additional patient information. For example, in an embodiment of the present invention, a user/patient enters blood pressure, blood sugar, pulse readings, and/or meal plan readings, on a mobile device, a terminal 110, in order to communicate the readings to his or her physician.

The software 160 obtains (S430) the data received at the terminal 110 at the secure, encrypted, HIPAA compliant server 130. In an embodiment of the present invention, to protect the privacy of a terminal 110 user, such as a patient, personal identification of a patient is associated by the software 160 with a medical record number of the patient.

The software 160 encrypts the data from the terminal 110 (S440). Upon encrypting the data, in embodiments of the present invention, the software 160 saves the data from the terminal 110 (S450) on a computer readable storage medium 150. In this manner, the software 160 meets HIPAA guidelines for securing patient information. In embodiments of the present invention, the software 160 stores all encrypted data in HL7 message files. In an embodiment of the present invention, the software 160 enables the computer readable storage medium 150 to generate HL7 messages for the electronic medical record of a given patient.

In an embodiment of the present invention, the software 160 determines whether the data received is within a preconfigured "acceptable" range and if not, sends an alert to the patient's care provider (S460), for example, by sending an electronic alert, such as a text or email, to the care giver terminal 170. Provided the software 160 transmits the patient data itself, it does so in an HL7 message file to comply with HIPAA standards. The software 160 can also make the data obtained from the terminal 110 as well as historical data that it saved on the computer readable storage medium, accessible to a user of a care giver terminal via a GUI.

The software 160 obtains a response from the care giver (S470), via a care giver terminal 170 and can retain this response on the server 130 and/or securely communicate the response to the terminal 110 (S480). In this manner, disease readings are monitored and managed by the physician, and he/she sees fit by sending return message to the patient regarding the readings. For example, in embodiments of the invention, the software 160 is interactive so that the physician can make recommendations to the patient for changes in medications, diet, and exercise to positively affect/improve his or her disease. As a result, the patient becomes very involved in his or her own health care, but not "tied" to his or her physician for multiple office visits.

In embodiments of the present invention, the software 160 can communicate a variety of data regarding a given patient to a physician. Because the server 130 can store medical data, including the electronic medical record, relating to the patient in a secure way, for example, by utilizing patient numbers instead of identifying information, encrypting the data, and creating HL7 messages, when a physician receives an alert and/or checks a patient's reported readings, he or she can also reference historical data on the server 130 as well as the patients' electronic medical record, also encrypted and secured on the server 130 in embodiments of the present invention. In an embodiment of the present invention, the software 160 displays the patient's medical data including medications relating to diabetes and hypertension with patient readings, including but not limited to, pulse pressure, weight, height. The availability of this complete information is helpful in correctly treating a patient for disease states.

As diet is also a contributing factor to diabetes and hypertension and maintaining a healthy diet helps treat these conditions, embodiments of the present invention can also assist in this dimension of health care. In an embodiment of the present invention, computer readable storage medium on the server (or accessible to the server) stores a pre-loaded diet plan for a given patient. When the patient utilizes the terminal 110, the software 160 can provide the user with meal plan information. From the care provider terminal 170, a nutritionist and/or dietician can make changes/suggestions to the patient and modify the plan.

Embodiments of the present invention enable the patient and provider to experience an instant communication. Although the server 130 provides security between the terminal 110 and the care provider terminal 170, from the patient and physician perspective, communications occur in real-time. FIG. 4A is a workflow 500 showing an aspect of an embodiment of the present invention from the perspective of a patient utilizing a terminal 110.

Referring to FIG. 4A, a patient utilizes a GUI on the terminal 110 to log into the application (S510), which can be understood as being created by computer code being executed by a processor at a server 130. Hence, the software enables the interactions of what is being referring to in this figure as the application. As seen in FIG. 4A, the patient logs onto the application at the terminal 110 (S510) and enters BP and Sugar Readings (S520) and provided that the terminal 110 is connected to a network (i.e., online), the data entered by the patient can be saved on the server 130 (S530a). In the event that the terminal 110 is not connected to a network, the data can be saved locally (S530b). Because of the manner described earlier in which the software 160 supplements and protects the data, the data is saved by the software 160 on the server 130 (S540a) and at what is perceived by a user as the same time, the data shows instantly on the care provider terminal 170 (S550a). With this information, the provider utilizes the care provider terminal 170 to update the medications of the patient (S560a), and, like the data entered at the terminal 110 by the patient, because of the back-end secure processing described earlier, the data entered by the provider displays "instantly" on the terminal 110 to the patient (S570a). Please note that in this embodiment of the present invention, the login of the user can be verified even without connectivity to the network and therefore, the computer program code that handles the verification is executed locally at the terminal 110. However, the verification functionality of the computer code can also be integrated into the code executed at the server 130.

Figure 21:
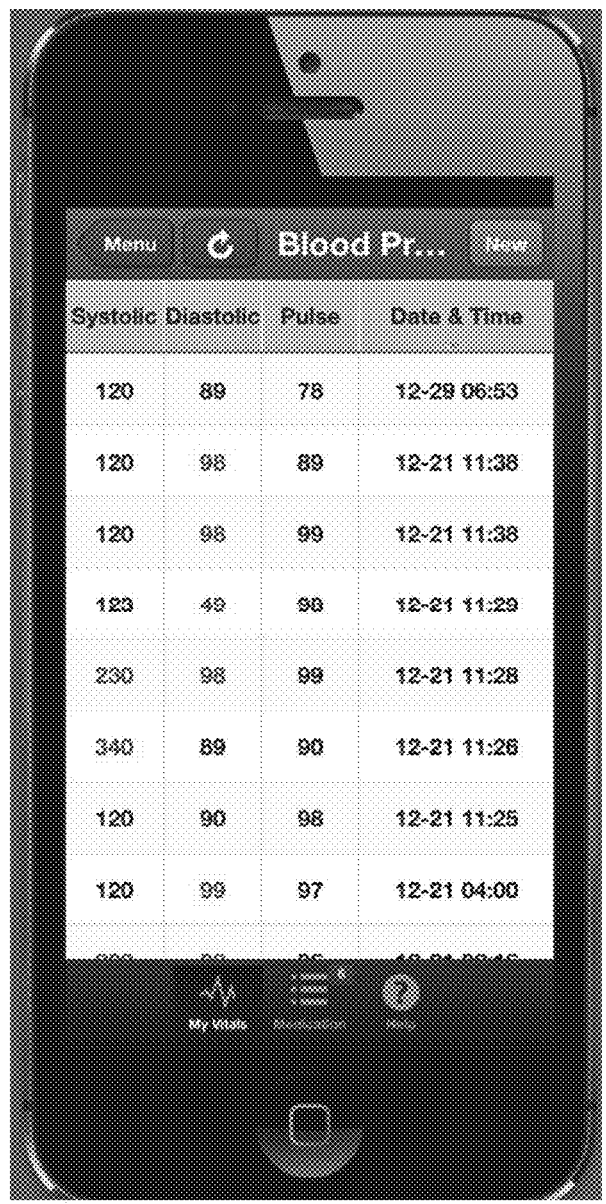

FIG. 4B is an aspect of a workflow 600 of an embodiment of the present application from the point-of-view of the provider. As seen in FIG. 4B, a provider accesses the invention by logging into a GUI (S610). When authorized by the software 160, the provider can view notifications for abnormal readings in the GUI of the care provider terminal 170 (S620). In response to these readings, the provider has the option of utilizing the software 160 to take a number of actions, including but not limited to, updating the medications of the patient (S630), checking for refills (S640), confirming a refill request with a patient (S650), posting new medication changes to a patient's account (S660), and/or deleting notifications and posting updates (S670). Please note that the order of the actions available to the care provider, as well as the actions themselves, as displayed in FIG. 4B, are meant as a non-limiting example. Referring to FIG. 21, in an embodiment of the present invention, this is an exemplary screenshot of a GUI viewable on terminal 110 displaying readings taken by a patient and highlighting abnormal blood pressure readings visually, in this case, in red.

To increase the security of the technique, a number of features are integrated into various embodiments of the present invention. Security features include, but are not limited to, providing accesses between the terminal 110, the server 130, and the care provider terminal 170 through an HTTPS protocol with a secured socket active certificate, locking a user out, whether a patient or a provider, after a set number of unsuccessful login attempts, refraining from storing patient-identifiable information on the terminal 110, enabling remote deactivation of the terminal 110 and/or the access of the terminal 110 to the server 130, through the care provider terminal 170 or at the server 130, enabling deactivation of the care provider terminal 170 and/or the access of the care provider terminal 170 to the server 130, at the server 130, and/or at another terminal, storing the MAC address of the terminal 110 in a resource accessible to the server 130 and enabling access to the server 130 only if the MAC address is recognized by the software 160, and/or storing data in encrypted databases in a secured server behind a firewall.

Figure 5:
FIG. 5 depicts an example of an exemplary graphical user interface (GUI) produced by an aspect of the present invention.
Figure 6:
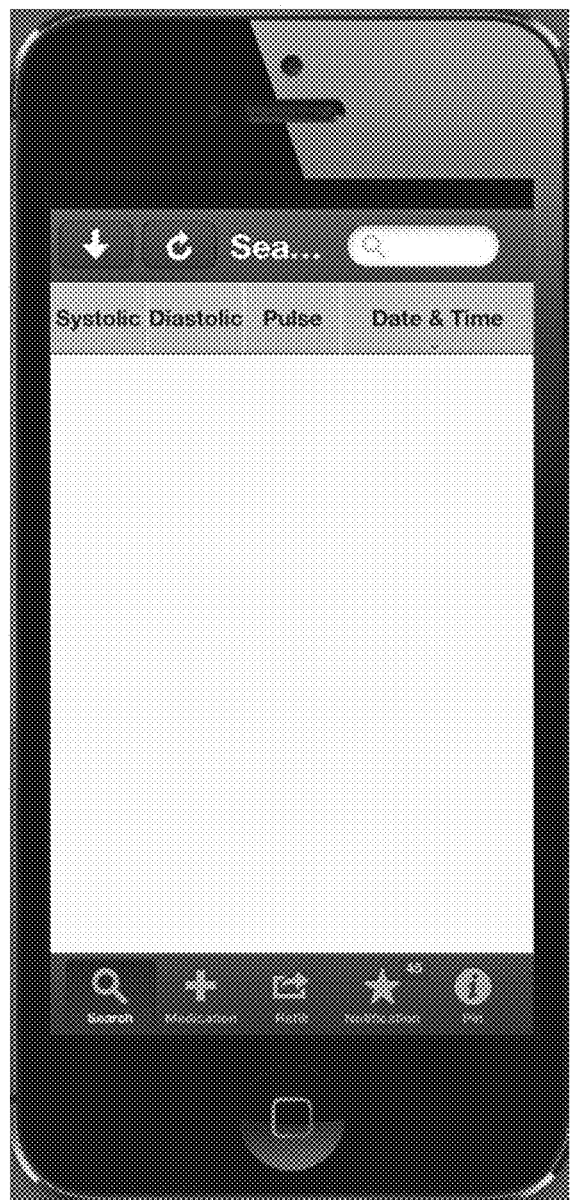
FIG. 6 depicts an example of an exemplary graphical user interface (GUI) produced by an aspect of the present invention.

In embodiments of the present invention, a factor that assists in facilitating communication between patients utilizing terminals and care givers utilizing terminals, are the graphical user interfaces provided by the software 160. An embodiment of the present invention provides a separate customized GUI (graphical user interface) for each user group, patients and physicians (this terms includes other care providers). The interfaces can be referred to as a Patient Dashboard and a Physician Dashboard. FIG. 5 is a screenshot of an embodiment of a Patient Dashboard, while FIG. 6 is a screenshot of an embodiment of a Physician Dashboard. Some features of various embodiments of these user interfaces, which are discussed in great details below, provide one or more of the following features: 1) data viewable on the Patient Dashboard is protected so that the patient name and MRN are not visible on the device; 2) through the Physician Dashboard, a care giver can take advantage of various reporting features available on the server 130; 3) background color, text, textbox and buttons are different colors and provide a professional, easy to understand look; 4) security measures enable a user of the Physician Dashboard to access data exclusive to his or her patients. The sections that follow discuss features of the Physician Dashboard and Patient Dashboard GUIs available in select embodiments of the present invention.

In an embodiment of the present invention, the Physician Dashboard has 5 tabs: Search, Medication, Refill, Notification, and Pin. Further embodiments of the present invention may include one or more of these tabs. In the embodiment discussed here, the Search tab allows the physician to locate a patient's data using the medical record number of that patient. The Medication tab allows the physician to enter current medications. Those medications will instantly populate the medication field on the Patient Dashboard. The Refill tab allows the physician to view refills the patient has requested through the medication field on the Patient Dashboard. The Notification tab alerts the physician to data that falls outside acceptable ranges for blood pressure, blood sugar and pulse. The Pin tab allows the physician to view a list of all the patients currently on the application, their names, MRNs and passwords. The Pin tab allows the physician to search for a patient using the MRN, first or last name. In embodiments of the present invention, the physician can view a patient's data in a variety of formats, including but not limited to, a daily format and/or an average weekly format. The Pin tab also enabled the physician to enter a new patient and delete or deactivate an existing patient.

In an embodiment of the present invention, the Patient Dashboard has 3 tabs: My Vitals, Medication and Help. Further embodiments of the present invention may include one or more of these tabs.

In an embodiment of the present invention, the My Vitals tab gives the patient the option to enter blood pressure, blood sugar or both. Once the data is entered in the appropriate fields, the patient has the option to Submit, Clear or Cancel the data. If the patient chooses to submit the data, software 160 obtains the data and handles it in a manner, as described in reference to FIG. 4, wherein the physician effectively receives it instantly. In some embodiments, the My Vitals tab has a list, sorted chronologically, by date and time, of all data the patient has entered. This feature allows the patient to view all the data and determine if there is a pattern with their blood pressure or blood sugar. If the patient is able to determine a pattern, then the patient is empowered to make changes in his or her treatment and/or lifestyle.

In an embodiment of the present invention, the Medication tab has a list of medications the patient is currently taking. The medication list is generated on the Physician Dashboard and can only be modified on the Physician Dashboard. Once a medication is entered on the Physician Dashboard, the patient is asked to accept the medication using a simple two step procedure. This feature ensures that the patient and physician are in agreement with the current medication list. The patient is also able to request refills using a simple two step procedure.

In an embodiment of the present invention, through the GUI that displays on the terminal 110, the patient has an option to select a particular medication and request a refill. When a patient makes this selection, the software 160 displays this request in the Physician Dashboard, on the care giver terminal 170.

The care provider can utilize the Physician Dashboard to indicate that the prescription is renewed. In this manner, a provider can track his or her patient's medications, and thus, track chronic issues more easily.

In an embodiment of the present invention, once the physician has renewed the prescription, the software 160 communicates this information to the patient by displaying an alert, for example, a Red alert, on the screen of the terminal 110 showing the old and the new updated med. When the patient utilizes an input device coupled or integrated into the terminal 110 to accept the medication update, the software 160 obtains this ascent and removes the alert. This quick method of asking for a refill helps a patient keep track of his or her meds as well as keep his or her blood pressure and blood sugar under control.

In an embodiment of the present invention, the Help tab is available to guide the patients through the application and lists common abbreviations used on the application. The Help tab also provides the website and e-mail should the patient need technical assistance. Any medical questions must be directed through the patient's physician.

As aforementioned, embodiments of the present invention can also be utilized to monitor the diet of a patient and to implement a nutrition plan. In an embodiment of the present invention, this diet-related aspect enables a user to utilize a drag and drop method in a GUI for characterizing a diet, including, but not limited to, choosing diet type, selecting from a list of possible or favorite food options, quantity, and time of day. The diet drags and drop screens can incorporate pictures, and text, as well as options to save or choose an item from favorite foods.

An embodiment of the invention can also incorporate further functionality into the user's GUI on a terminal 110 such as tabs under a main Diet tab, including but not limited to Favorites, and Schedule. As a user selects a diet plan to plan meals and/or enters meals that he or she is consuming, the software 160 will determined the calories of the meal choices by accessing a mapping table on a computer readable storage medium accessible to the server 130 and/or internal to the server 130.

An embodiment of the present invention can include an Alert or Notifications feature, which will display messages to users from the dietitian and/or nutritionist who is monitoring the activity of the patient. Similarly, the present invention can also include a New or Recommendations feature that displays new food options that are preferred to help control blood sugar and blood pressure.

By entering data regarding meal choices into a terminal 110, the software 160, upon encrypting and structuring the data in a manner that complies with HIPAA guidelines and protects the privacy of the patient, can make this data accessible to a nutritionist and/or dietician on a care provider terminal 170. Specifically, in an embodiment of the present invention, by interacting with a Diet tab on a GUI, the patient enables the software 160 to obtain messages and number of calories consumed, to be passed on to the dietitian. To aid the patient and the dietician in understanding the content, the GUI provides color coded alerts based on calorie consumption and other nutritional information such as: protein, fat carbohydrates, etc. These colors alerts are configured to indicate how well the patient is following a pre-configured meal plan, which is accessible to the software 160 executed on the server so that the software can access the data entered as well as the plan data and determine whether the user is complying with the plan and identify discrepancies.

In embodiments of the present invention, the aforementioned favorite list features may also feature a "NEW" tab in the Diet category. When a user selects this tab, the software 160 connects to internal and/or external memory resources to query whether there are new products on the market to check if there are new products on the market that are comparable to something on the favorite list of a given patient.

As mentioned earlier, embodiments of the present invention store historical data securely on memory resources accessible to the software 160 executing on the server 130. Historical data related to nutritional entries is also available in relation to diet entries. Thus, in the client interface, in embodiments of the present invention, a user can view his or her History, retrieved from the saved data, on a separate tab, including having access to meal plans for a given period, such as the last ten days.

To further increase ease of use, in embodiments of the present invention, the Diet tab includes animations that reflect a patient's progress at following a plan. For example, a character can appear when the software 160 determines that an intake obtained from the terminal 110 is out of an acceptable range.

Embodiments of the present invention include a computer-implemented method, a computer program product, and a system for enabling streaming communication between a patient and a provider, the method comprising. In some embodiments of the present invention, program code executed by one or more processors executes an interface on a remote care provider device, where the interface is configured to receive and to access data of patients associated with a care provider and to communicate the patients. The program code obtains, at a secure HIPAA compliant server, from a mobile device over an Internet connection, data related to the health state of a patient selected from the patients, where a first portion of the data is obtained upon submission, via an interface on the mobile device and a second portion of the data is obtained from a secured location on the mobile device, wherein the second portion of data was submitted through the interface when the mobile device was not connected to the secure HIPAA compliant server over the Internet and stored by the mobile device in the secured location of the mobile device, where the secure HIPAA compliant server comprises a processor and a computer readable medium that stores an electronic medical record comprising a medical record number of the patient, historical medical data for the patient associated with the medical record number, and contact information for the care provider for the patient, wherein the contact information is utilized to enable streaming communication between the patient and care provider. The program code (of the secure HIPAA compliant server) associates a timestamp with the data, associating the data with the medical record number of the patient. The program code (of the secure HIPAA compliant server) writes the data to the computer readable medium in an encrypted format. The writing includes program code (of the secure HIPAA compliant server) encrypting the data, the program code (of the secure HIPAA compliant server) converting the data to a first set of HL7 embedded portable document format (PDF) message files, and the program code (of the secure HIPAA compliant server) writing the first set of HL7 embedded portable document format (PDF) message files into the electronic medical record. The program code determines whether the data is in a pre-configured range. The program code determines, based on the contact information, that the patient is associated with the care provider. Responsive to determining that the data is not in the pre-configured range and that the patient is associated with the care provider, the program code utilizes the contact information to transmit, automatically, a real-time alert in the encrypted format over a wireless communication channel to the remote care provider device, where the alert is automatically displayed in the interface, where the displaying enables the care provider to utilize the interface to access, over the Internet, certain of the data related to the health of the patient and the historical medical data stored on the computer readable medium of the secure HIPAA compliant server, and where the alert comprises personally identifiable patient data transmitted as an HL7 message file. Responsive to the alert, the program code obtains a response from the wireless device associated with the care provider of the patient and associates the response with the medical record number of the patient and encrypts and writes the response to the computer readable medium in the encrypted format, where the response comprises a medical recommendation based on at least one of: the data and/or a portion of the historical medical data. The program code displays, on the mobile device, instantaneously upon obtaining, the medical recommendation, based on the streaming communication, where the medical recommendation comprises a diet plan. Based on obtaining the diet plan, the program code executes a query on a memory resource selected from the group consisting of an external memory resource and an internal memory resource. Responsive to the query, the program code obtains information describing one or more products compatible with the diet plan. The program code displays the information on the mobile device.

In some embodiments of the present invention, program code executing on one or more processors executes an interface on a remote care provider device, where the interface is configured to receive and to access data of patients associated with the care provider and to communicate the patients. The program code obtains, at a secure HIPAA compliant server, from an interface on a mobile device over an Internet connection, data related to the health state of a patient selected from the patients, where the secure HIPAA compliant server comprises a processor and a computer readable medium that stores an electronic medical record comprising a medical record number of the patient, historical medical data for the patient associated with the medical record number, and contact information for the care provider for the patient, wherein the contact information is utilized to enable streaming communication between the patient and care provider. Program code executing on a processor of the secure HIPAA compliant server associates a timestamp with the data and associates the data with the medical record number of the patient. The program code executing on the processor of the secure HIPAA compliant server writes the data to the computer readable medium in an encrypted format, where the writing comprises: encrypting the data, converting the data to a first set of HL7 embedded portable document format (PDF) message files, and writing the first set of HL7 embedded portable document format (PDF) message files into the electronic medical record. The program code (executing on the one or more processors) determines whether the data is in a pre-configured range. The program code determines, based on the contact information, that the patient is associated with the care provider. Responsive to determining that the data is not in the pre-configured range and that the patient is associated with the care provider, the program code utilizes the contact information to transmit automatically a real-time alert in the encrypted format over a wireless communication channel to the remote care provider device, wherein, based on determining that the wireless device associated with the care provider is online, the alert is automatically displayed in the interface, and wherein based on determining that the wireless device associated with the care provider is not online, the alert is retained at a secured location and displayed in the interface when the wireless device associated with the care provider is online, where the displaying enables the care provider to utilize the interface to access, over the Internet, certain of the data related to the health of the patient and the historical medical data stored on the computer readable medium of the secure HIPAA compliant server, where the alert comprises personally identifiable patient data transmitted as an HL7 message file. Responsive to the alert, the program code obtains a response from the wireless device associated with the care provider of the patient and associates the response with the medical record number of the patient and encrypts and writes the response to the computer readable medium in the encrypted format, where the response comprises a medical recommendation based on at least one of: the data, a portion of the historical medical data. The program code displays, on the mobile device, instantaneously upon obtaining, the medical recommendation, based on the streaming communication, where the medical recommendation comprises a diet plan. Based on obtaining the diet plan, the program code executes a query on a memory resource selected from the group consisting of an external memory resource and an internal memory resource. Responsive to the query, the program code obtains information describing one or more products compatible with the diet plan. The program code displays the information on the mobile device.

In some embodiments of the present invention, the program code converts the response to a second HL7 message files before writing the data to the computer readable medium.

In some embodiments of the present invention, the historical medical data includes historical data related to the health of the patient obtained over a pre-configured period of time.

In some embodiments of the present invention, the data comprises at least one of a blood sugar reading or a blood pressure reading.

In some embodiments of the present invention, the medical recommendation comprises at least one prescription.

In some embodiments of the present invention, the data comprises a record of food consumed by the patient over a given period of time.

In some embodiments of the present invention, the patient data comprises vital signs of the patient and the medical recommendation comprises a provider intervention.

In some embodiments of the present invention, the patient data comprises dietary habits of the patient and the medical recommendation comprises a provider intervention.

Figure 25:
FIG. 25 is an example of a PDF that can be generated and retained in embodiments of the present invention.

In some embodiments of the present invention, the program code generates, based on the data related to the health state of a patient and the medical recommendation, an HL7 embedded PDF document. The program code integrates the HL7 embedded PDF document into the electronic medical record. FIG. 25 is an example of a PDF that can be generated by program code in some embodiments of the present invention. Not only does the program code in the interface generate the PDF summary, but this PDF can be integrated, by the program code, into an electronic medical records (EMR) system. The data creates a dual integrated interface with CMV and EMR. Program code in embodiments of the present invention can also obtain (and select and query) data from the EMR system through a CCDA Care Continuity Document.

An embodiment of the present invention includes the use of a mobile device, which will allow close connection between the physician and the patient. The patient will enter the blood pressure, blood sugar, pulse and meal plan readings into their mobile device in a manner including, but not limited to, manually, utilizing an input method, or by voice activation. The GUI utilized for entry and the back end system is usable with any mobile device or computer, which has access to a communications network, such as the Internet. An embodiment of the present invention is a web based application. An embodiment of the present invention is HIPAA compliant, secure, and/or the data is encrypted before it saves to any computer readable storage medium. In an embodiment of the present invention, a central server stores all patient data, and creates an HL7 message file to be ready to transport to the patient's medical record. One advantage of the present invention is that it eliminates a patient's paper readings and enabled patients to review their medications and request refills electronically.

FIGS. 7-21 are screenshots that are examples from a GUIs of an embodiment of the present invention. These screenshots are offered as a non-limiting example to illustrate the ease of interaction with the system for a user.

Figure 7:
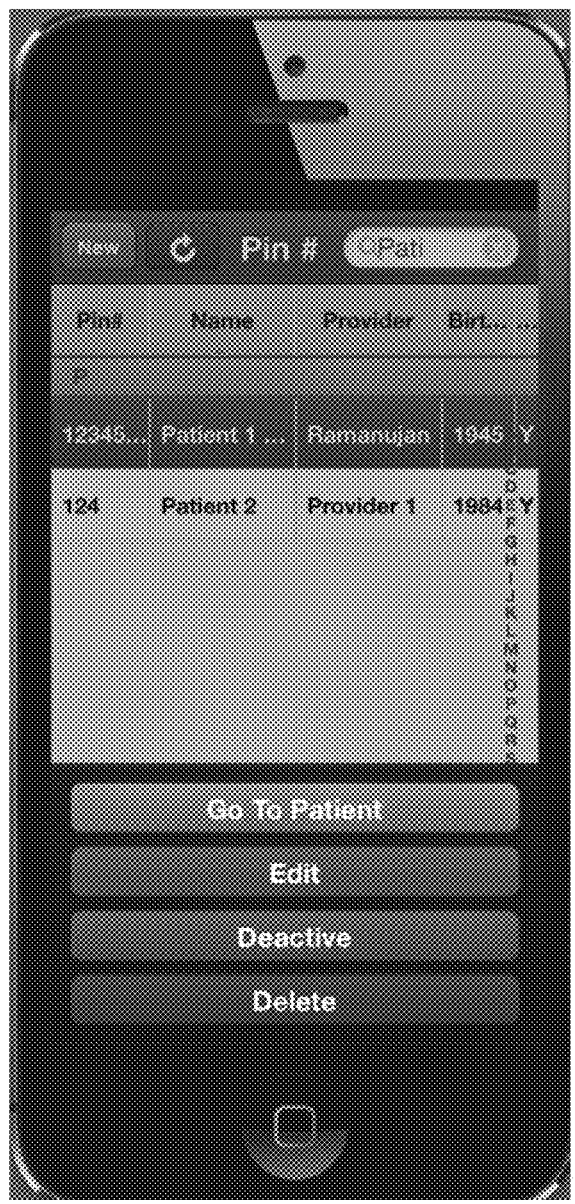
FIGS. 7-21 depict examples of user interfaces available for user input and interaction in an embodiment of the present invention.

FIG. 7 is an example of a Provider Admin Screen with patient information hidden.

Figure 8:
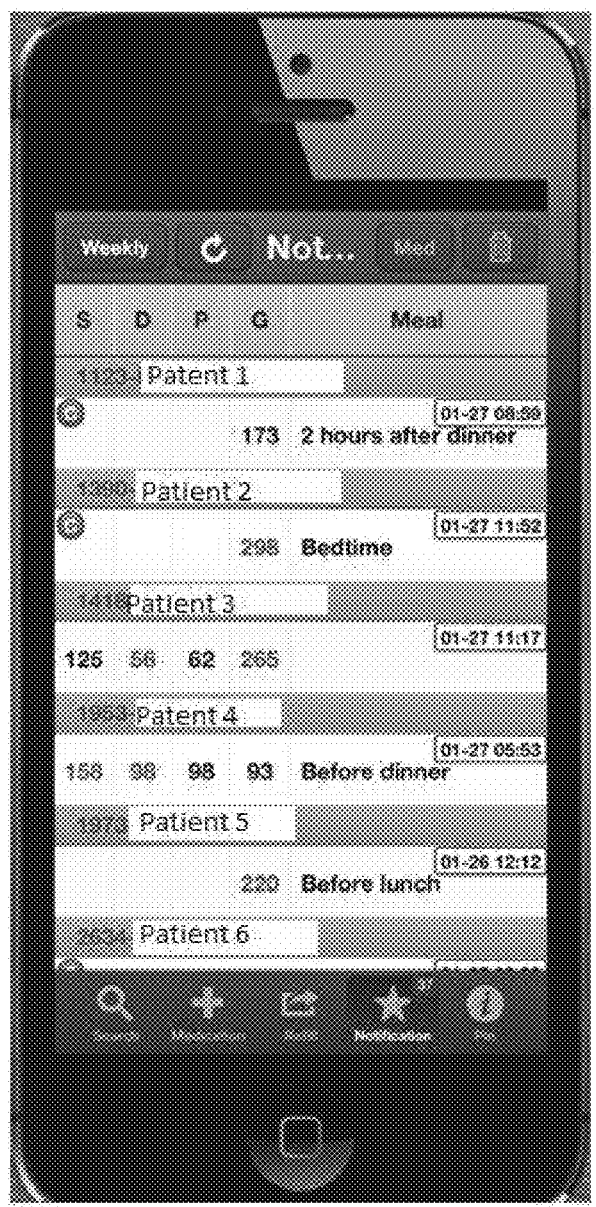

FIG. 8 is a Notification Screen with Alerts from Patients with Comments and Date Sorted for Provider monitoring.

Figure 9:
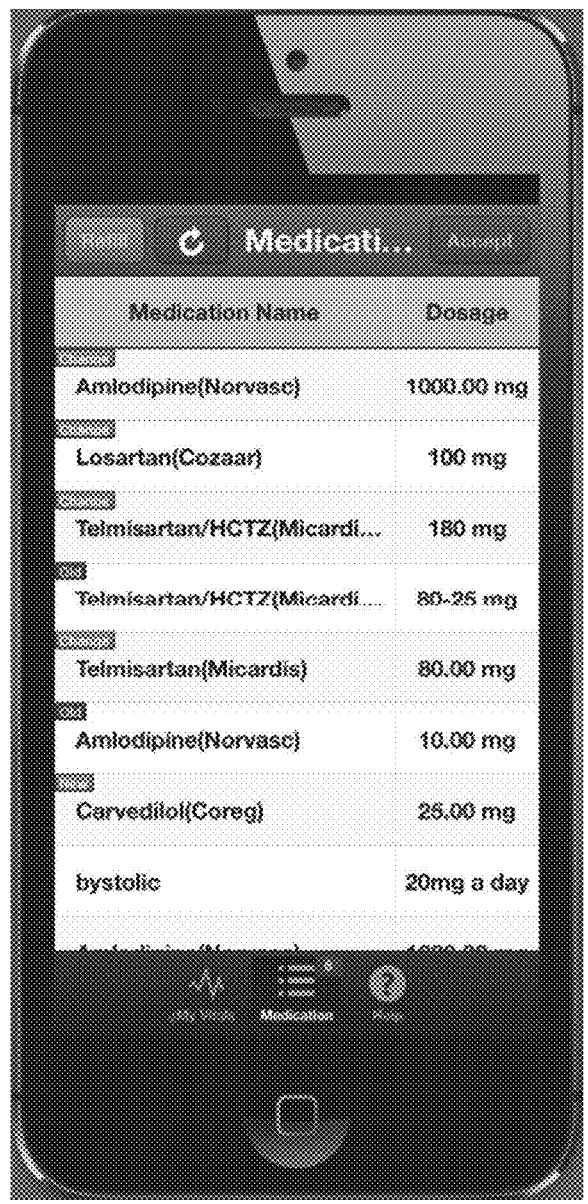

FIG. 9 is an example of Refill Request functionality available to the patient, as well as direct instant communication on Provider side for each Refill request. One click to request a refill is a unique option for the patient. This shows an alert on the provider's side that a patient is looking for a medication refill. After the refill is updated, the patient receives a message back in the application notifying them about the same.

Figure 10:

FIG. 10 is a Medication form for the Provider to add or edit a medication.

Figure 11:
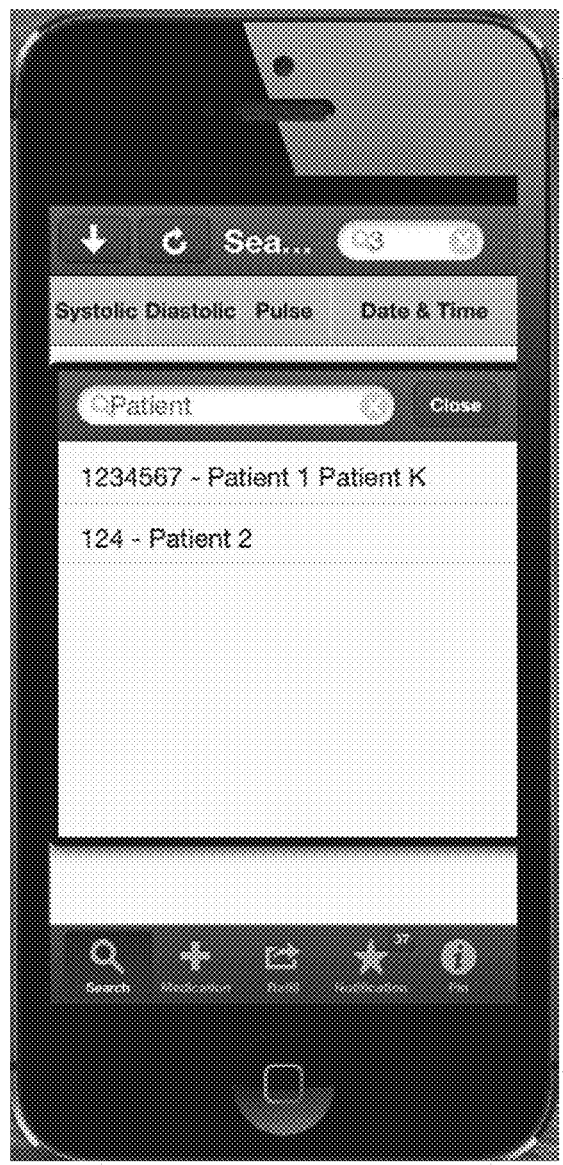

FIG. 11 illustrates the Search Option available to search for patients using PIN #s, Last names or First Names, discussed earlier.

Figure 12:
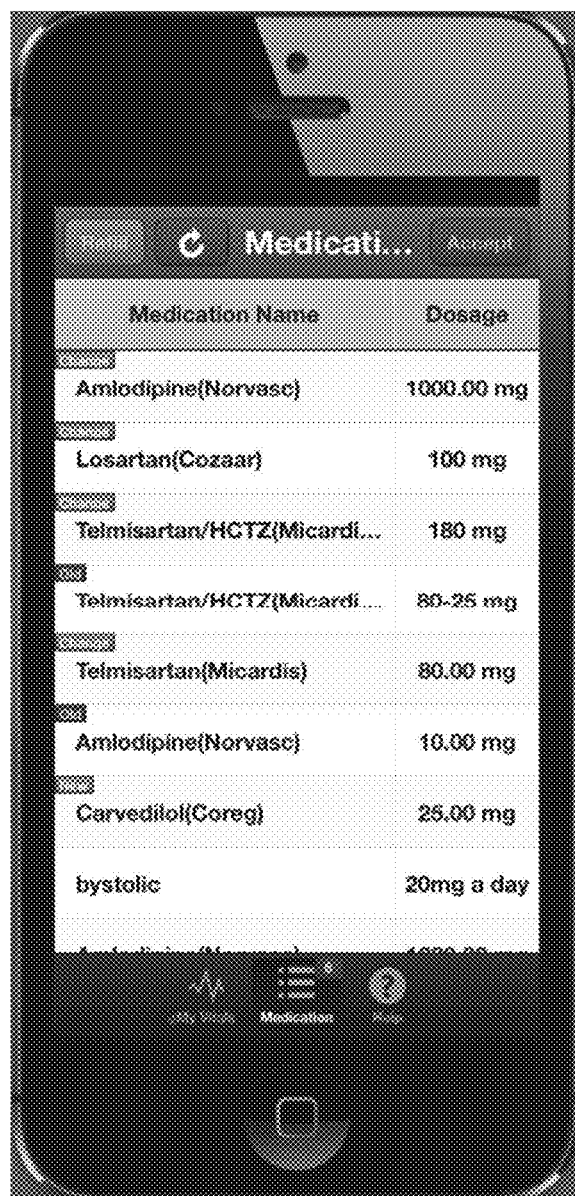

FIG. 12 illustrates how Medication Details pop up on Patient Side.

Figure 13:

FIG. 13 is a Help Screen on the Patient side to provide easy instructions to input the variables.

Figure 14:

FIG. 14 illustrates how Patients can enter their vital signs into the GUI.

Figure 15:
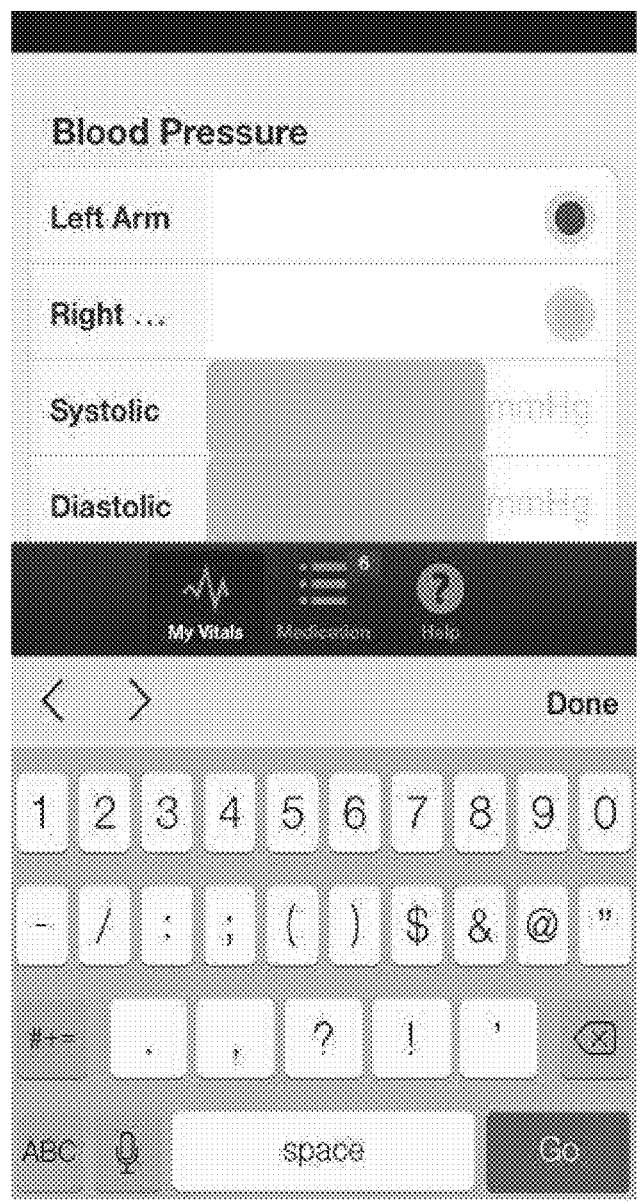

FIG. 15 illustrates a Keyboard as well as voice activated screen to type or talk into the screen to input vital signs.

Figure 16:
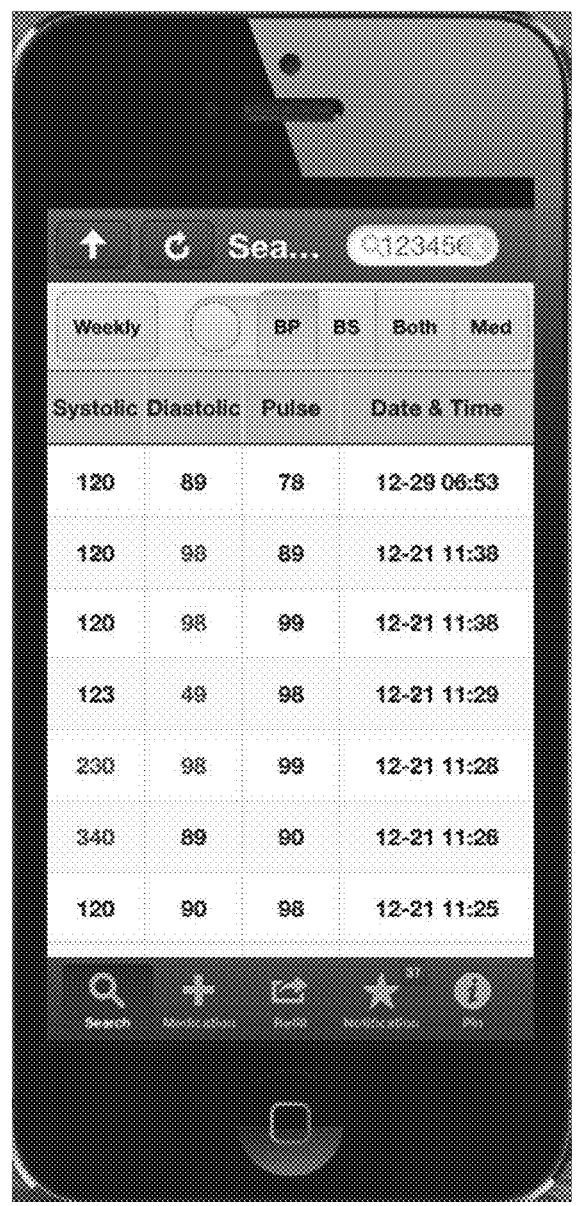

FIG. 16 is a Blood Pressure Recording/Reading screen in a table grid format, with date with sorting feature available and details available on double click.

Figure 17:
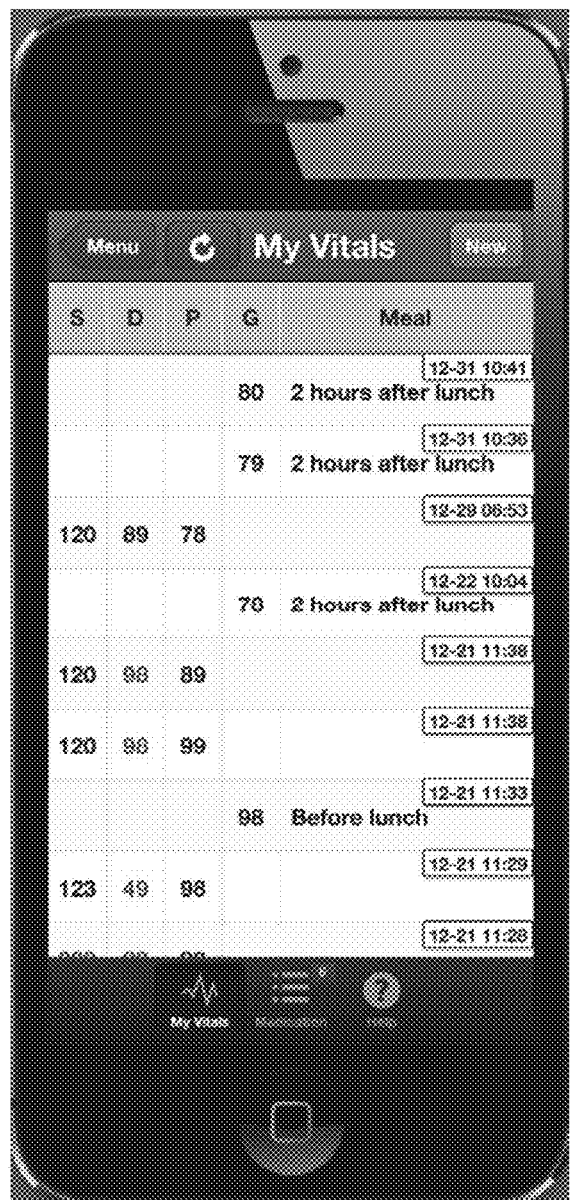

FIG. 17 is a Blood Sugar Recording/Reading screen in a table grid format, with date with sorting feature available and details available on double click.

Figure 18:
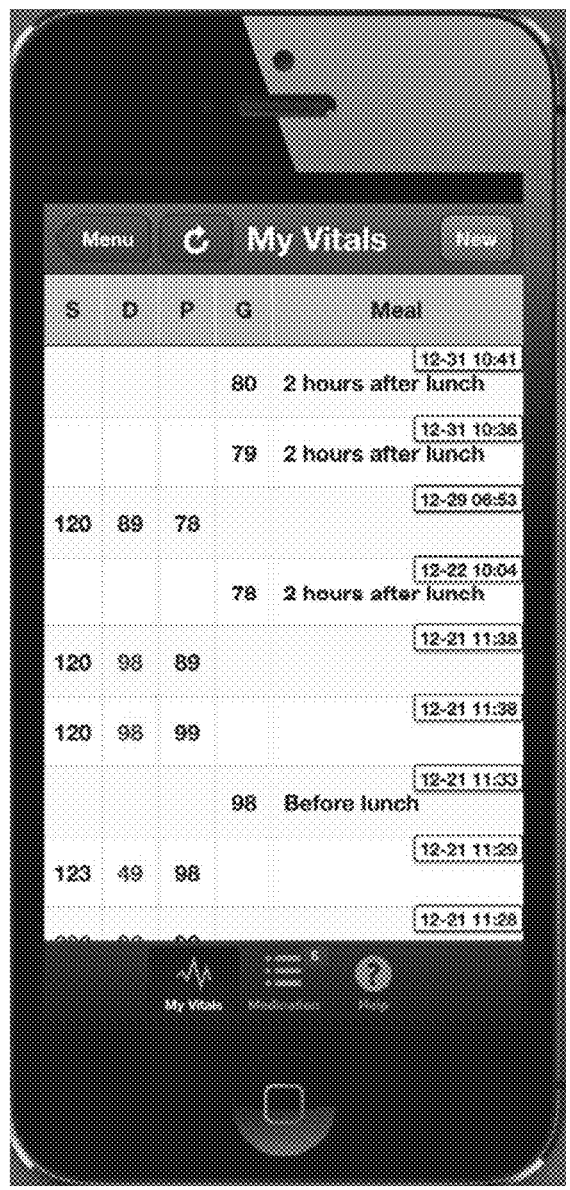

FIG. 18 is a Blood Pressure & Blood Sugar Recording/Reading screen in a table grid format, with date with sorting feature available and details available on double click.

Figure 19:
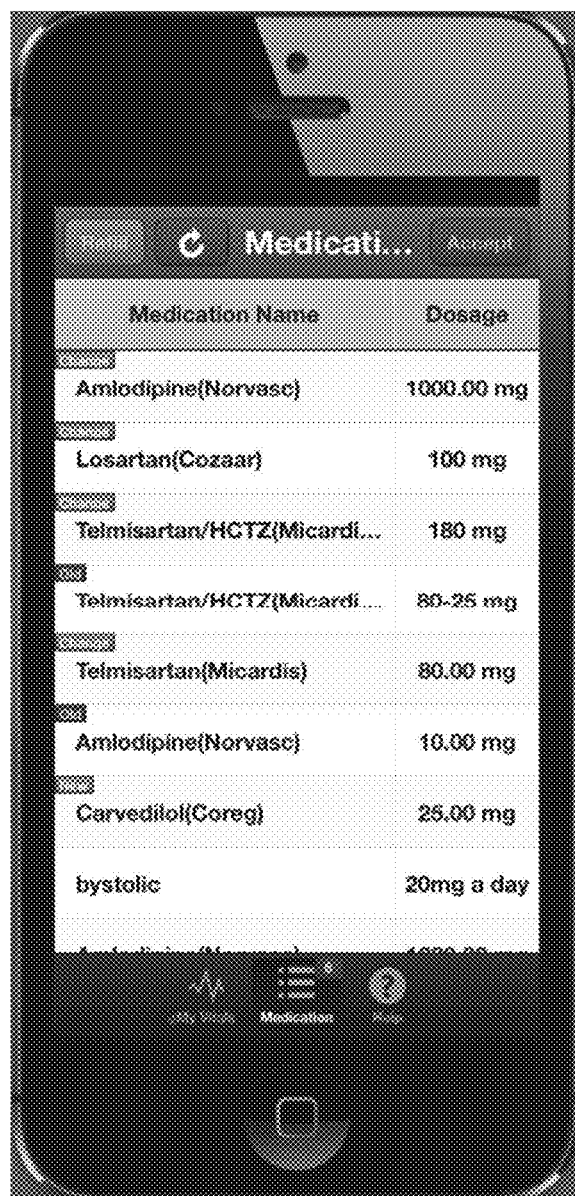

FIG. 19 is a Patient Medication List shown on a screen with Change, Old medications to accept refills requested by the patients.

Figure 20:

FIG. 20 depicts Blood Pressure, Blood Sugar and Both options available for recording on the Patient Dashboard screens.

FIG. 21 shows a listing of blood pressure readings to demonstrate that detail is available, based on date and time of the reading, through interfaces generated by the program code in embodiments of the present invention.

Figures 22, 23:
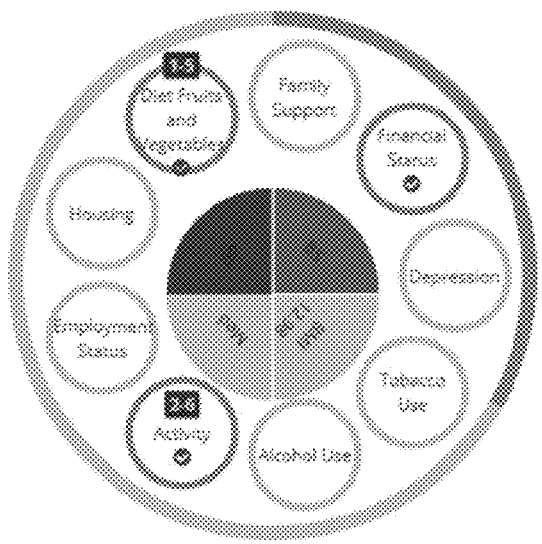
FIGS. 22-24 depict various aspects of user interfaces and functionalities comprising these interfaces, as generated by program code in some embodiments of the present invention.

As discussed earlier, the details and timing of notifications to both care providers as well as to patients (as a streaming communication) coupled with security and privacy features provide various advantages over existing method of enabling electronic communications between care providers and patients. FIG. 22 is a dashboard that provides, at a glance, a summary of statistics for a given care provider. In this example, the program code generates a screen that shows a number of patients (assigned to the care provider), a number of active patients (e.g., those who have interacted in various ways with the care provider through the application, including, in one example, those who have requested prescription refills through the application). The interface generated by the program code also displays the number of readings in the last year (from utilizing various Internet of Things (IoT) devices, including those integrated into mobile devices, to monitor patients), notifications, refills, average patient age, number of care providers, and the last PDF that was generated by the application. An example of the type of PDF that can be generated by an embodiment of the present invention is FIG. 25.

As understood by one of skill in the art, the IoT is a system of interrelated computing devices, mechanical and digital machines, objects, animals and/or people that are provided with unique identifiers and the ability to transfer data over a network, without requiring human-to-human or human-to-computer interaction. These communications are enabled by smart sensors, which include, but are not limited to, both active and passive radio-frequency identification (RFID) tags, which utilize electromagnetic fields to identify automatically and to track tags attached to objects and/or associated with objects and people. Smart sensors, such as RFID tags, can track environmental factors related to an object or an area, including but not limited to, temperature and humidity. The smart sensors can be utilized to measure temperature, humidity, vibrations, motion, light, pressure and/or altitude. IoT devices also include individual activity and fitness trackers, which include (wearable) devices or applications that include smart sensors for monitoring and tracking fitness-related metrics such as distance walked or run, calorie consumption, and in some cases heartbeat and quality of sleep and include smartwatches that are synced to a computer or smartphone for long-term data tracking. Because the smart sensors in IoT devices carry unique identifiers, a computing system that communicates with a given sensor can identify the source of the information. Although in some embodiments of the present invention, users actively register IoT devices for utilization by the program code, in some embodiments of the present invention, the program code could automatically discover possible IoT devices and request confirmation from the user. Within the IoT, various devices can communicate with each other and can access data from sources available over various communication networks, including the Internet. Certain IoT devices can also be placed at various locations and can provide data based in monitoring environmental factors at the locations. In embodiments of the present invention, program code executing on one or more processors can obtain various values (readings) provided, in real-time, as well as historically, by one or more IoT devices.

One interface generated by the program code in embodiments of the present invention (and consistently updated as more information is provided through a patient interface) is a graphical interface referred to as a healthy wheel. FIG. 23 provides an example of the healthy wheel provided by the program code in various embodiments of the present invention. A healthy wheel is a snapshot that displays, in real-time, and updates, in real-time, a snapshot of overall patient health. The healthy wheel is a combination of multiple data variables that allow a provider to understand a patient better, not just using clinical vital signs, but also by utilizing socio demographic factors that are relevant to the patient. Program code in embodiments of the present invention can obtain data that it populates on the health wheel from a variety of heterogeneous sources, including electronic medical records, socioeconomic data related to geographic areas, and information provided by a patient (on entry through the application and also, from secured data). In order to populate the healthy wheel, the program code collects, both actively and passively, various data.

As illustrated in FIG. 23 an activity portion of the healthy wheel captures data from daily patient activity. The activity for a given patient can be designed by a healthcare provider or other care giver. This activity is designed for the patient, and the average activity is considered to calculate the health state of the given patient. In embodiments of the present invention, the program code can determine whether an individual is meeting activity thresholds both based on manual entry by a patient though a patient interface and/or by passively capturing this data, for example, from an IoT device of the patient, including but not limited to an activity tracker. In some embodiments of the present invention, program code assesses the activity of a given patient based on different factors, including but not limited to, a number of minutes, and assessment of a level of activity, the age or age range of the patient, and/or the medical issues of the patient. The activity can be established on a minimum scale activity, which can include participation of the patient in physical activities, including home activity, walking, etc. The activity can also be broken down into stages and can be managed by a medical provider, through the interface including but not limited to, a physiologist.

In some embodiments of the present invention, the healthy wheel also captures the socio-economic status of a given patient. This factor can be a rating of 1-4 (for example) on a Townsend scale (based on the Townsend index, a measure of material deprivation within a population). The determination of the socio-economic status of a given patient can be determined by the program code based on pulling data from various sources, including patient records, but can also be based on polling a patient for data. The Townsend scale is based on four variables: employment (or, rather, lack of employment of people above 16 within a given household), car ownership (or rather lack of ownership), home ownership (or rather lack of ownership), and household (over)crowding. This information is available in the program code based on patient entry and/or medical records, in some embodiments of the present invention. Thus, the program code can provide this healthy wheel representation to include this actor.

In some embodiments of the present invention, the healthy wheel interface also includes a value for depression, which is binary. This value is based upon the medical records of the individual.

In some embodiments of the present invention, the healthy wheel interface also includes a value representing tobacco use, which can be binary, but can also be a value on a set scale, including but not limited to, whether the patient is a smoker, not a smoker, an ex-smoker, a heavy smoker, and/or an infrequent (low) smoker. In some embodiments of the present invention, the specific smoking habits of an individual can be obtained to populate this element in the interface.

Certain other elements of the healthy wheel can also be binary values, in some embodiments of the present invention, the healthy wheel displays the employment status of the patient (e.g., employed or unemployed), the housing situation of the patient (e.g., independent or dependent), and/or the alcohol usage of the patient (e.g., yes or no). In some embodiments of the present invention, the program code can provide more details for these elements of the healthy wheel. As aforementioned, the information utilized to populate the healthy wheel can come from various data sources, including the electronic medical records of the patient, entry by the patient through and interface, and/or publicly available data sources, including but not limited to, social media.

In some embodiments of the present invention, the healthy wheel also includes the diet of the individual (as provided by the patient as well as medical records). Elements that comprise the diet can include but are not limited to fruits and vegetables consumed. In some embodiments of the present invention, a health provider, who is a dietician, can count a minimum of vegetables, 2, 3 4, or whether the patient consumes foods at all (yes or no), can view a heathy seven scale, based on readings, including, but not limited to weight, whether the patient has diabetes, (diet is denominator). The care provider can determine whether the patient needs a therapeutic lifestyle change and can establish and implement a baseline requirement for the patient. In embodiments of the present invention, any adjustments that the care giver provides in the healthy wheel can be transmitted in real-time to the patient.

In some embodiments of the present invention, the healthy wheel also includes whether the patient has family support (in maintaining a health state). This can be a binary value (yes or no) and can also include details about the living situation of the patient, including but not limited to, whether the support provider cooperative, remote, and/or in-house.

Notifications can populate in various parts of the health wheel such that the care provider can see where a patient has strayed from a baseline. In some embodiments of the present invention, the program code displays certain parts of the wheel in different colors in order to draw attention to areas that include deviations.

Figure 24:
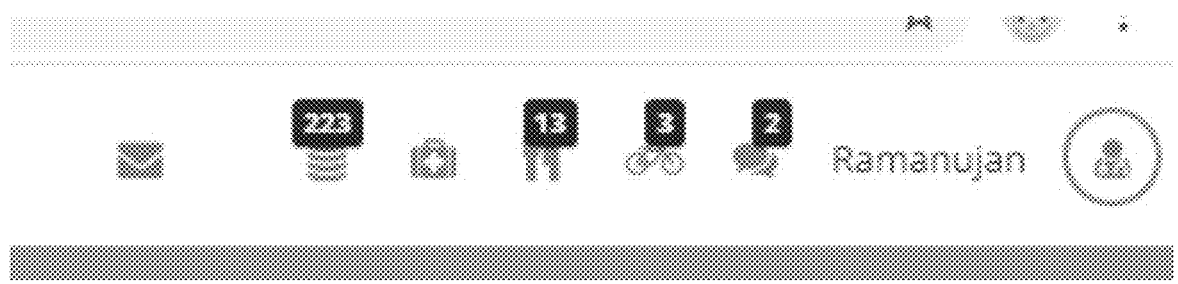

As discussed above, in various embodiments of the present invention, the program code provides alerts to a provider, through an interface. FIG. 24 is an example of the level of detail in which alerts can be provided in an interface in some embodiments of the present invention. As illustrated in FIG. 24, the program code in embodiments of the present invention enables providers to see population health specifics and allows providers to contact support without leaving the application interface. A healthcare provider (user) can click on a given alert, navigate directly to a more detailed record (including but not limited to a healthy wheel interface), and can contact an additional individual linked to the patient's record for assistance. For example, a physician could utilize the application to contact a dietician and vice versa. When either the physician or the dietician makes an adjustment in the interface, responsive to the alert, the patient can receive this change (e.g., medical recommendation) in real time.

In some embodiments of the present invention, the program code can anticipate (predict) a deviation that would result in an alert to the healthcare provider through the interface, in advance of an actual event. To this end, the program code monitors the user and by utilizing data collected by available (e.g., registered) IoT devices, and can apply machine learning algorithms to model the user's health patterns and to generate a user health profile, establishing a baseline (which can be automatic or can be set, in advance, for a patient, by a healthcare provider, through an interface, which can include the healthy wheel). The program code can train these algorithms, based on patterns for the patient (or across all patients). Some embodiments of the present invention utilize a machine learning training system to perform cognitive analyses of sensor and IoT data and/or electronic medical records, to generate a user health profile (e.g., baseline) in embodiments of the present invention. Program code can obtain data in embodiments of the present invention from one or more personal devices (e.g., IoT devices, sensors, personal health trackers, physical activity trackers, smart watches, etc.), which the user can be utilizing while a session is active on a computing device, as well as from entry values by the user and/or from electronic medical records of the user.

Machine learning (ML) solves problems that cannot be solved by numerical means alone. In this ML-based example, program code extracts various features/attributes from training data (e.g., medical records), which can be resident in one or more databases. In some embodiments of the present invention, the training data can comprise historical medical and general health data (such as in the categories in the healthy wheel) of the user and/or of a group of users. The features are utilized to develop a predictor function, h(x), also referred to as a hypothesis, which the program code utilizes as a machine learning model. In identifying various features/attributes (e.g., patterns) in the training data, the program code can utilize various techniques including, but not limited to, mutual information, which is an example of a method that can be utilized to identify features in an embodiment of the present invention. Further embodiments of the present invention utilize varying techniques to select features (elements, patterns, attributes, etc.), including but not limited to, diffusion mapping, principal component analysis, recursive feature elimination (a brute force approach to selecting features), and/or a Random Forest, to select the features. The program code can utilize a machine learning algorithm to train the machine learning model (e.g., the algorithms utilized by the program code), including providing weights for the conclusions, so that the program code can prioritize various anticipated health events, in accordance with the predictor functions that comprise the machine learning model. The conclusions can be evaluated by a quality metric. By selecting a diverse set of training data, the program code trains the machine learning model to identify and weight various attributes (e.g., features, patterns) that correlate to various medical events. Based on modeling the user's behavior and medical data, the program code can determine (for example) whether temporal sensor data represents an established pattern, or whether a deviation can be anticipated.

Figure 26:
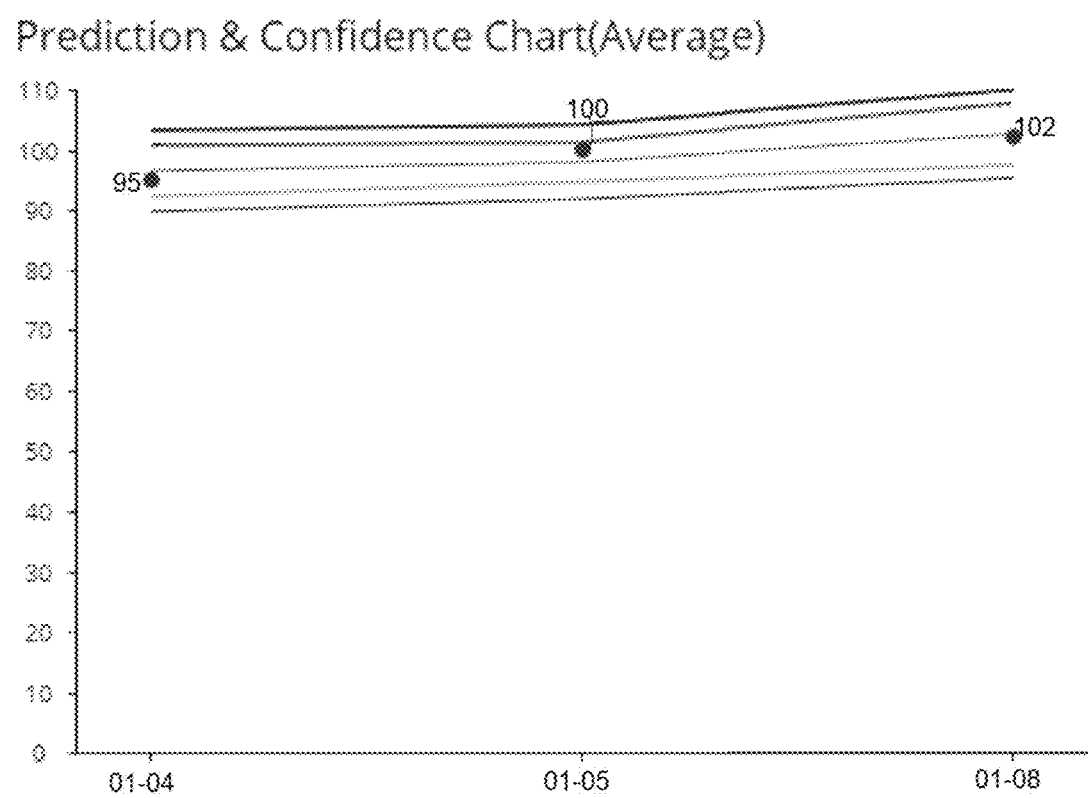
Figure 27:
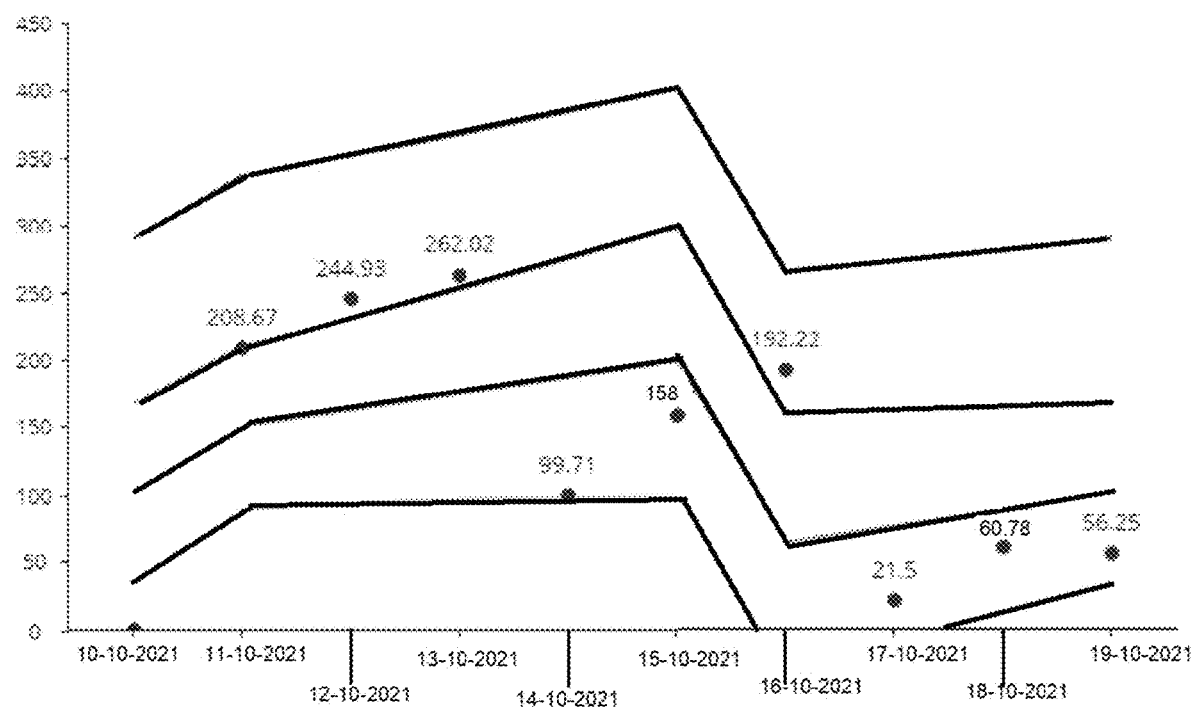
Figure 28:
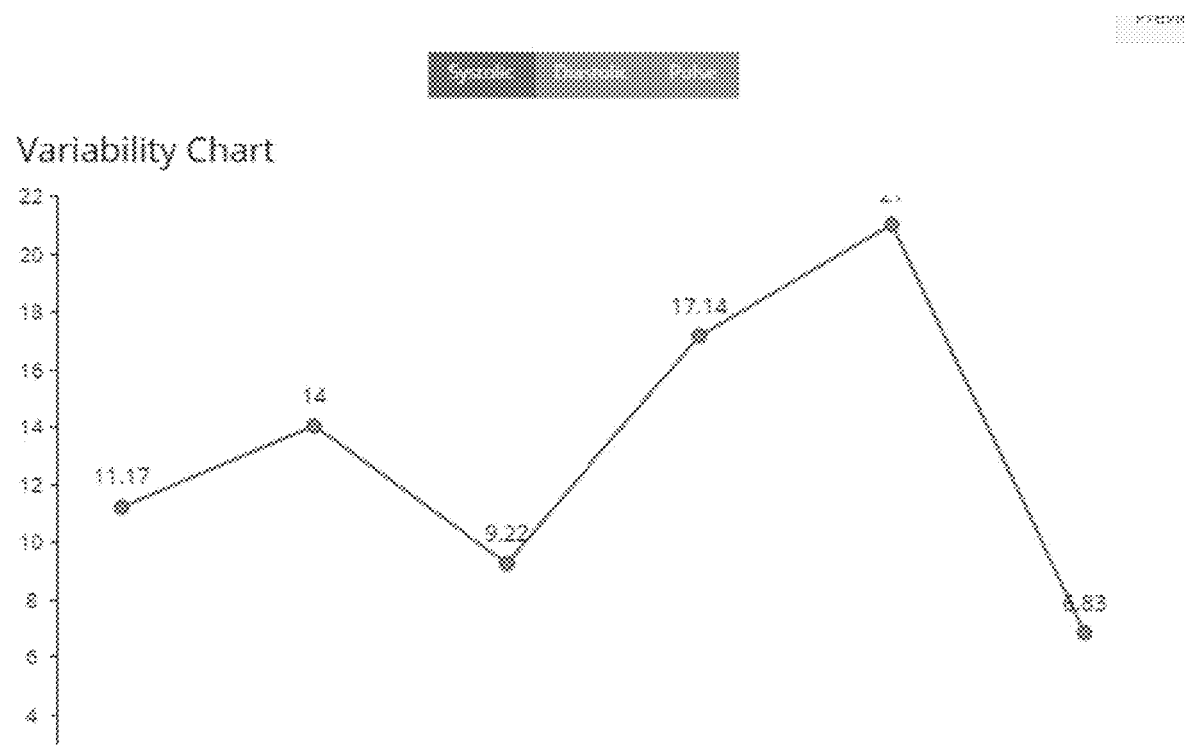

In some embodiments of the present invention, the program code executed by one or more processors, utilizes machine learning to predict and provide confidence level statistic within the interface in order to provide variability data to healthcare providers. FIGS. 26-28 are examples of predictions and statistics that can be generated in the interface utilized by healthcare providers in embodiments of the present invention. As illustrated in FIGS. 26-28, the program code in some embodiments of the present invention generates prediction and confidence interval statistics including, but not limited to, automatically generating Real Variability, Standard Deviation, and/or Coefficient of Variation.

Figure 29:
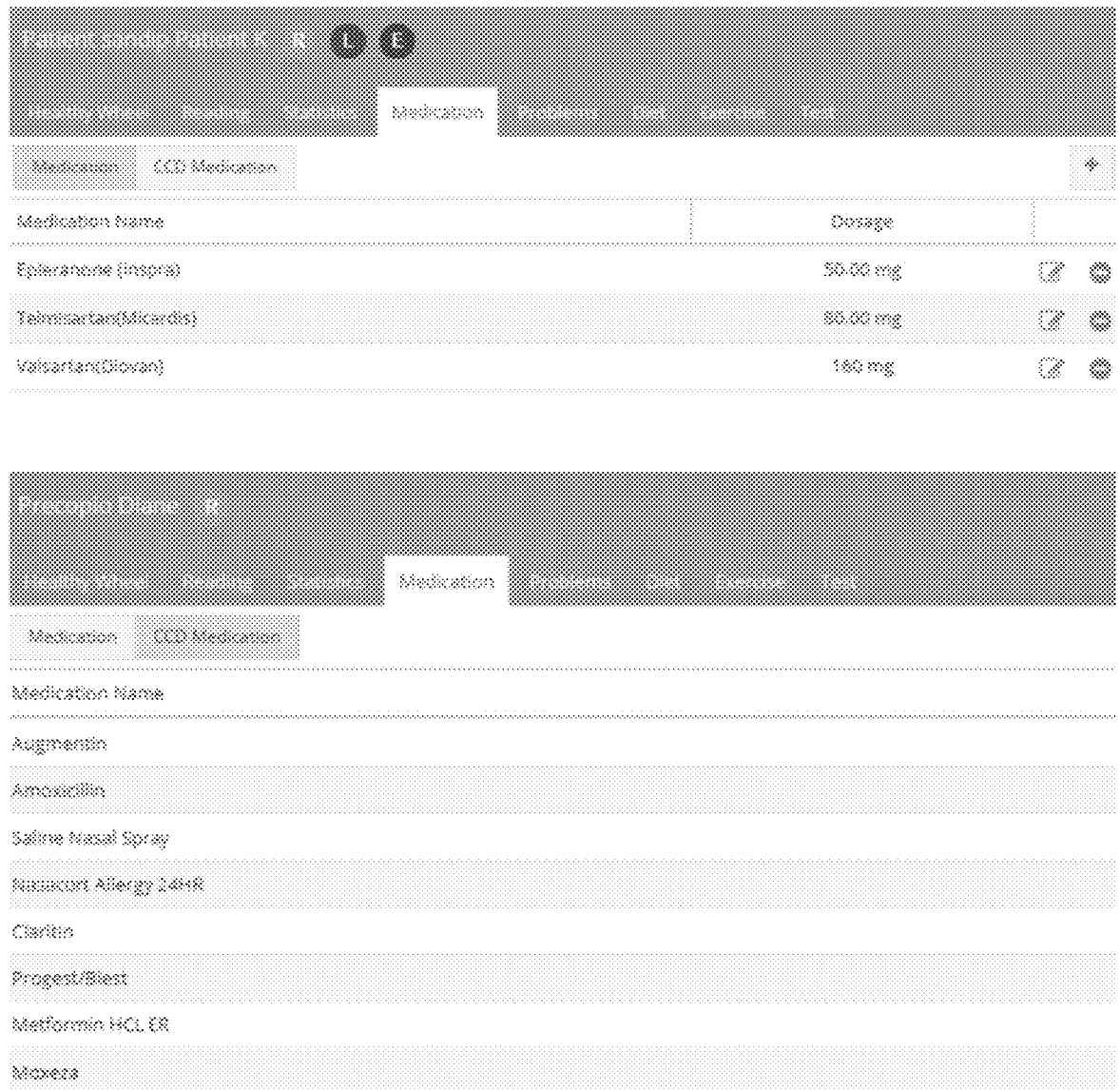

The interface generated by the program code in some embodiments of the present invention also provides a user with a view of reconciled medications by integrating data from the CCDA EMR documents. This allows providers to make a comprehensive treatment plan and alleviates errors on the part of providers, which could have adverse health consequences. FIG. 29 provides an example of a medication reconciliation interface generated by program code in some embodiments of the present invention.

As discussed above, in some embodiments of the present invention, the program code can provide a recommendation responsive to a medical issue that is related to the diet of a patient. To that end, FIG. 30 is an example of an interface generated by the program code in embodiments of the present invention that enables a care provider user to see data in a structured way. In both an interface provided by the program code to the patient, as well as to the provider, the user can scan foods, as well as save functionalities being recommended by the dietitian. Based on recommendation provided by the dietician, the program code in the interface can make specific "smart" recommendations that factor in health goals set by professionals (and in concert with the recommendations).

Figure 31:
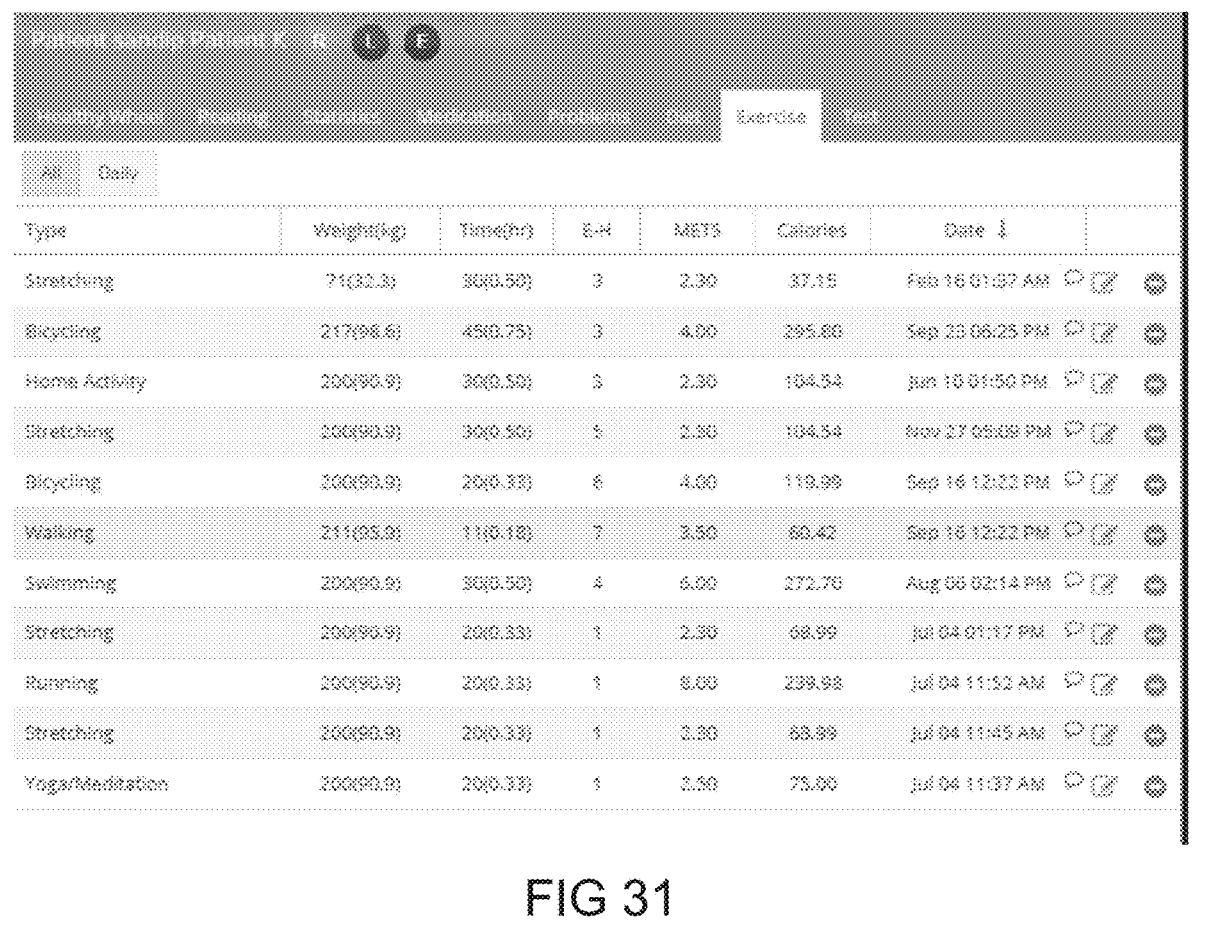

As a health profile of a given patient includes exercise, in some embodiments of the present invention, the program code generates an interface by which not only can a patient enter exercise, but the provider can also view the exercise (and annotate) in a comprehensive manner FIG. 31 is an example of this interface. Through this exercise functionality, providers receive data in a more structured way to understand activity function for patients. As with the diet functionality, based on goals and recommendations set by a healthcare provider, the program code can make recommendations to the patient to fulfill goals (these can be understood as smart recommendations based on the program code utilizing algorithms). In some embodiments of the present invention, the exercise interface can be automatically populated on the patient side because the patient device running the application interfaces with an IoT device of the patient which tracks physical activity of the patient.

Figure 33:
Figure 34:
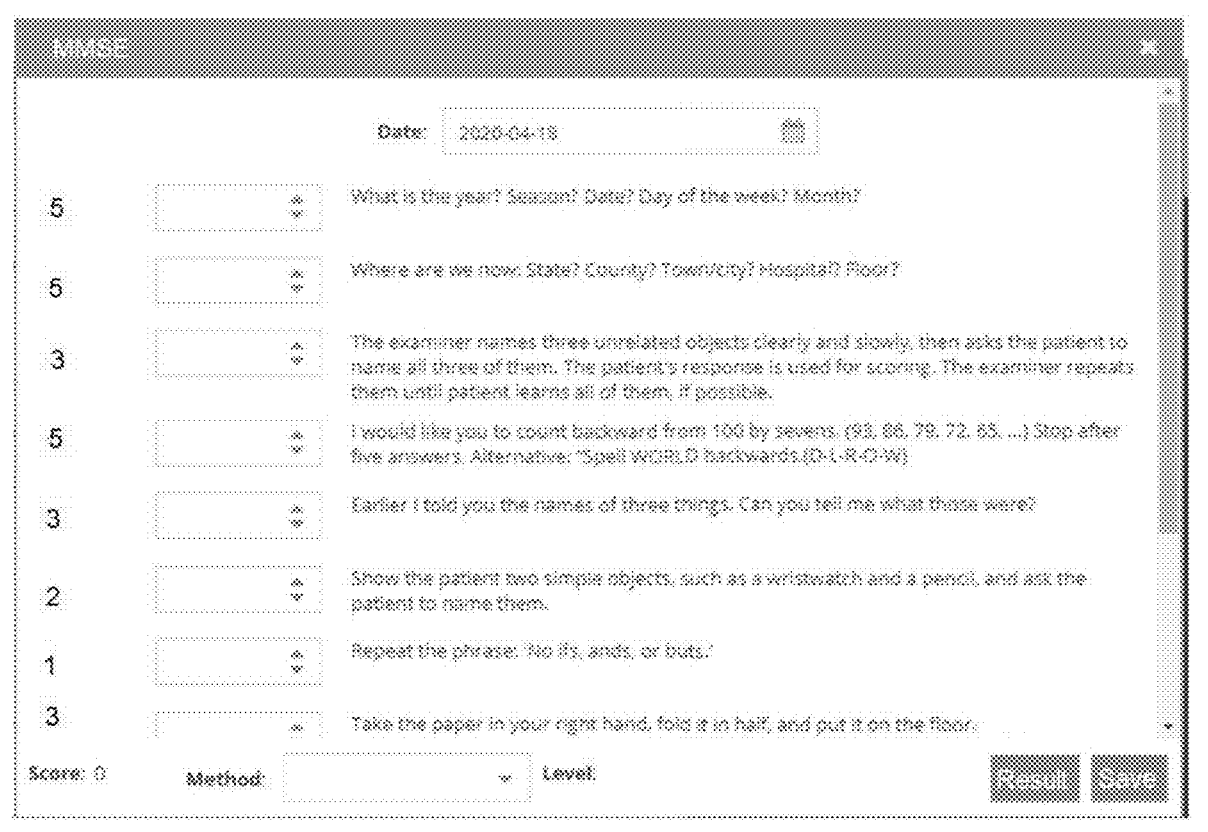

FIG. 32 shows how a patient can provide information about his/her/their sleep patterns through the patient interface, which is then available to the healthcare provider. This questionnaire is a sleep test, and the program code correlates the blood pressure of the patient (via medical records and/or an IoT device and/or patient entry with the patient's blood pressure and blood sugar data. FIG. 33 is a similar interface in some embodiments of the present invention, but it is related to stress, and it also allows the provider to correlate this data with blood pressure and blood sugar. As seen in FIG. 34, in some embodiments of the present invention, the program code provides an interface (in the application) to measure mental health of a patient utilizing mini-mental state examiner (MMSE) examinations.

Figure 35:
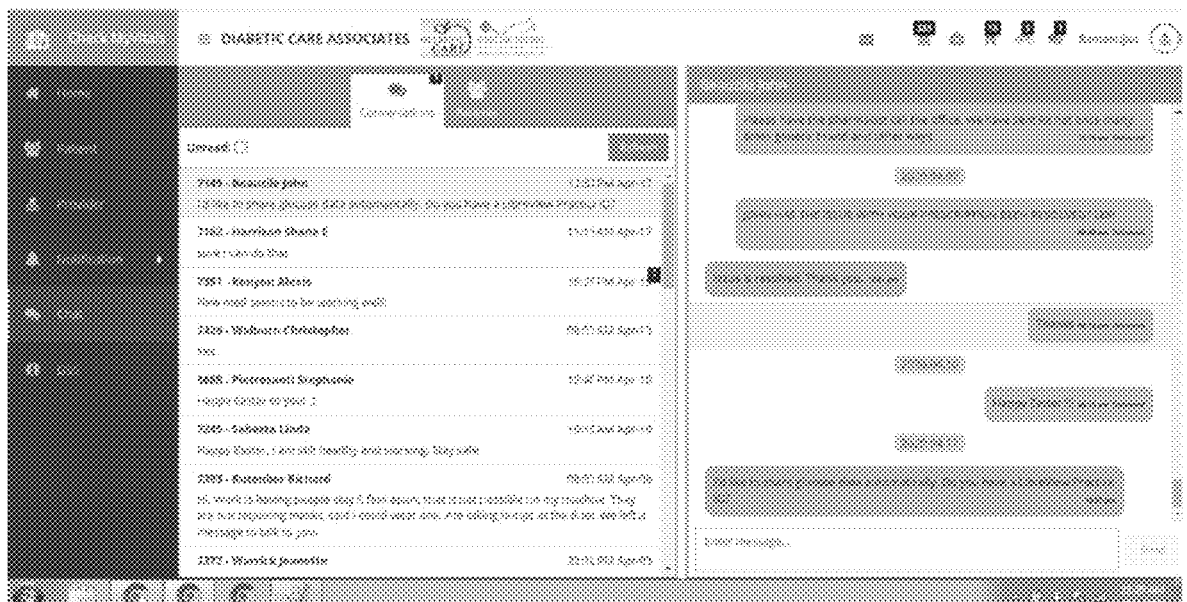
FIG. 35 illustrates a chat feature generated by the program code in embodiments on the present invention by which a care provider and a patient (and/or multiple care providers with and without the patient) can participate in an encrypted chat.

Streaming communication provided by the application (both to the provider and the patient) includes encrypted messaging between provider and patient. For example, some embodiments of the present invention include an encrypted chatroom, as illustrated in FIG. 35, where the program code encrypts communication such that they cannot be intercepted and are secure.

Figure 37:

When utilizing embodiments of the present invention to make a medical recommendation, the provider has various internal resources to refer to. FIGS. 36-37 are two of these types of resources. While FIG. 36 shows decision support, FIG. 37 is a guidelines document. Treatment guidelines saved on a resource accessible to the application are updated regularly.

Below, Example 1 is a recitation of an embodiment of at least one aspect of the present invention.

Example 1

Thirty-three percent of the population has been diagnosed with hypertension and 25.8 million Americans are diagnosed with Type I or II Diabetes; 1.9 cases per year. Example 1 of the present invention addresses this problem. A more effective way to monitor patient's w/hypertension and diabetes, occurs when patients can check their own readings and receive tight physician management through application The present invention is a physician driven application for their patients to monitor disease states in the comfort of their homes/office/school. Patients take their readings and send them in real time to their physician for interpretation and treatment via secure encrypted server.

This invention is an improvement on what currently exists. This is a physician driven application for their patients to monitor disease states in the comfort of their homes/office/school. Patients take their readings and send them in real time to their physician for interpretation and treatment via secure encrypted server.

The patient's medical data including medications relating to diabetes and hypertension are displayed with patient readings along pulse pressure, weight, height-all integral parts of treating a patient for disease states In application screen, medical information exclusive to patients is sent to physicians for interpretation and recommendation.

The Version of The Invention Discussed Here Includes:
1. An application for a mobile device
2. Offered exclusively by the physician to his/her own patients
3. HIPAA compliant
4. Patient data goes through secure encrypted server
5. Monitor patients with Diabetes and Hypertension in real time
6. Tight physician management of diseases
7. Patient data and outcomes easily integrated into patient's electronic medical record
8. Eliminates office Visits
9. Patients can send multiple readings every day and are being monitored more closely The invention is used to improve and tighten up physician management of Diabetes and Hypertension (5&6) by using mobile device technology (1) that is offered and sold exclusively by the physician to his/her own patients (2). The patient can send multiple readings every day to his/her provider (9) the readings will be date/time stamped and is send through a secure encrypted (4) HIPAA compliant server (3)which is easily integrated into the patient electronic medical record (7) and eliminates office visits (8) for the patient.

After the blood pressure and blood sugar readings are inputted manually into the mobile device by the patient, there is a button to send the data to the secure server for review by the physician. The personal identification of each patient utilizes the medical record number of the patient. The diseases readings are then monitored and managed by the physician, and he/she sees fit by sending return message to the patient regarding the readings In standard medical practice, specializing in Diabetes and Hypertension all elements are necessary for full medical analysis and treatment of disease states.

The software written includes all the elements necessary to maximize the best outcome for the patient and physician. Any change or shuffling of elements could severely affect the health care of the patient.

The patient (user) records his or her own blood sugar and or blood pressure readings, those readings are date/time stamped and then the patient sends them to the physician for interpretation and management of their disease states. It is interactive software so that the physician can make recommendations to the patient for changes in medications, diet, and exercise to positively affect/improve their disease. The patient becomes very involved in their own health care, but not "tied" to their physician for multiple office visits.

Accordingly, a small sample of combinations set forth in Example 1 are the following:
A1. A method for improving communication between a patient and a provider, the method comprising: obtaining, by a processor, data related to the health state of a patient; associating, by the processor, a timestamp with the data, encrypting the data and writing the data to a computer readable medium; determining, by the processor, whether the data is in a pre-configured range; responsive to determining that the data is not in the pre-configured range, sending an alert to a client; and obtaining a response from the client and writing the response to the computer readable medium, wherein the response comprises a medical recommendation based on the data.

A2. The method of A1, further comprising converting the data to a first HL7 message file before writing the data to the computer readable medium.

A3. The method of A1, further comprising converting the response to a second HL7 message file before writing the data to the computer readable medium.

A4. The method of A1, further comprising writing the data to an electronic medical record associated with the patient.

A5. The method of A1, wherein the alert comprises the data and supplemental data retrieved from the computer readable medium.

A6. The method of A5, wherein the supplemental data comprises historical data related to the health of the patient obtained over a pre-configured period of time.

A7. The method of A1, wherein the data comprises at least one of a blood sugar reading or a blood pressure reading.

A8. The method of A1, wherein the medical recommendation comprises at least one prescription.

A9. The method of A1, wherein the data comprises a record of food consumed by the patient over a given period of time.

A10. The method of A9, wherein the medical recommendation comprises a diet plan.

B1. A computer system for improving communication between a patient and a provider, the computer system comprising: a memory; and a processor in communications with the memory, wherein the computer system is configured to perform a method, said method comprising obtaining, by the processor, data related to the health state of a patient; associating, by the processor, a timestamp with the data, encrypting the data and writing the data to a computer readable medium; determining, by the processor, whether the data is in a pre-configured range; responsive to determining that the data is not in the pre-configured range, sending an alert to a client; and obtaining a response from the client and writing the response to the computer readable medium, wherein the response comprises a medical recommendation based on the data.

B2. The computer system of claim B1, the method further comprising converting the data to a first HL7 message file before writing the data to the computer readable medium.

B3. The computer system of claim B1, the method further comprising converting the response to a second HL7 message file before writing the data to the computer readable medium.

B4. The computer system of B1, the method further comprising writing the data to an electronic medical record associated with the patient.

B5. The computer system of B1, wherein the alert comprises the data and supplemental data retrieved from the computer readable medium.

B6. The computer system of B1, wherein the supplemental data comprises historical data related to the health of the patient obtained over a pre-configured period of time.

B7. The computer system of B1, wherein the data comprises at least one of a blood sugar reading or a blood pressure reading.

B8. The computer system of B1, wherein the medical recommendation comprises at least one prescription.

C1. A computer program for improving communication between a patient and a provider, the computer program product comprising: a computer readable storage medium readable by a processing circuit and storing instructions for execution by the processing circuit for performing a method comprising: obtaining, by the processor, data related to the health state of a patient; associating, by the processor, a timestamp with the data, encrypting the data and writing the data to a computer readable medium; determining, by the processor, whether the data is in a pre-configured range; responsive to determining that the data is not in the pre-configured range, sending an alert to a client; and obtaining a response from the client and writing the response to the computer readable medium, wherein the response comprises a medical recommendation based on the data.

C2. The computer program of claim C1, the method further comprising: converting the data to a first HL7 message files before writing the data to the computer readable medium; converting the response to a second HL7 message files before writing the data to the computer readable medium; and writing the data to an electronic medical record associated with the patient in the computer readable medium.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components and/or groups thereof.

The corresponding structures, materials, acts, and equivalents of all means or step plus function elements in the descriptions below, if any, are intended to include any structure, material, or act for performing the function in combination with other elements as specifically noted. The description of the technique has been presented for purposes of illustration and description but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The invention claimed is:

1. A computer-implemented method comprising:
   executing interface on a remote care provider device, wherein the interface on the remote care provider device is configured to receive and to access data of patients associated with a care provider and to communicate with the patients;
   authenticating the remote care provider device based on obtaining an entry in the interface on the remote care provider device;
   based on the authenticating, registering the remote care provider device to enable communications over a wireless communication channel between the remote care provider device and a secure HIPAA compliant server;
   obtaining, at the secure HIPAA compliant server, from an interface on a mobile device over an Internet connection, data related to a health state of a patient selected from the patients, wherein the secure HIPAA compliant server comprises a processor and a computer readable medium that stores an electronic medical record comprising a medical record number of the patient, historical medical data for the patient associated with the medical record number, and contact information for the care provider for the patient, wherein the contact information is utilized to enable streaming communication between the patient and the care provider;

associating, by one or more processors of the secure HIPAA compliant server, a timestamp with the data, associating the data with the medical record number of the patient;

writing, by the processor of the secure HIPAA compliant server, the data to the computer readable medium in an encrypted format;

determining, by the one or more processors, whether the data is in a pre-configured range;

determining, by the one or more processors, based on the contact information that the patient is associated with the care provider;

responsive to determining that the data is not in the pre-configured range and that the patient is associated with the care provider, utilizing the contact information to transmit automatically a real-time alert in the encrypted format over the wireless communication channel to the remote care provider device, wherein the remote care provider device comprises a wireless device associated with the care provider, and wherein, based on determining that the wireless device associated with the care provider is online, the alert is automatically displayed in the interface on the remote care provider device, and wherein based on determining that the wireless device associated with the care provider is not online, the alert is retained at a secured location and displayed in the interface on the remote care provider device when the wireless device associated with the care provider is online, wherein the displaying enables the care provider to utilize the interface on the remote care provider device to access, over the Internet, certain of the data related to the health of the patient and the historical medical data stored on the computer readable medium of the secure HIPAA compliant server, wherein the alert comprises personally identifiable patient data transmitted as an HL7 message file;

responsive to the alert, obtaining a response from the wireless device associated with the care provider of the patient and associating the response with the medical record number of the patient and encrypting and writing the response to the computer readable medium in the encrypted format, wherein the response comprises a medical recommendation based on at least one of: the data, a portion of the historical medical data; and displaying, on the mobile device, instantaneously upon obtaining, the medical recommendation, based on the streaming communication.

2. The computer-implemented method of claim 1, wherein the medical recommendation comprises a diet plan.

3. The computer-implemented method of claim 1, further comprising:
based on obtaining the medical recommendation, executing a query on a memory resource selected from the group consisting of an external memory resource and an internal memory resource; and responsive to the query, obtaining information describing one or more products compatible with the medical recommendation; and displaying the information on the mobile device.

4. The computer-implemented method of claim 3, further comprising:
converting the response to a second HL7 message file before writing the data to the computer readable medium.

5. The computer-implemented method of claim 1, wherein the data comprises at least one of a blood sugar reading or a blood pressure reading.

6. The computer-implemented method of claim 1, wherein the medical recommendation comprises at least one prescription and wherein the data comprises a record of food consumed by the patient over a given period of time.

7. The computer-implemented method of claim 1, wherein the data related to the health state of a patient is selected from the group consisting of: socioeconomic information, mental health status, tobacco use, employment status, housing, alcohol use, dietary information, and family support.

8. The computer-implemented method of claim 1, wherein the interface on the remote care provider device in which the alert is automatically displayed comprises a dashboard, wherein the dashboard provides the alert and a snapshot of a current heath condition of the patient.

9. The computer-implemented method of claim 8, wherein the current health condition of the patient displayed in the dashboard comprises factors, wherein at least one factor selected from the group consisting of: socioeconomic information, mental health status, tobacco use, employment status, housing, alcohol use, dietary information, and family support.

10. The computer-implemented method of claim 1, wherein the interface on the remote care provider device in which the alert is automatically displayed comprises a notification in a consolidated view of all patients of the care provider.

11. The computer-implemented method of claim 10, further comprising:
selecting, in the interface on the remote care provider device, the notification; and
based on obtaining the selection, displaying, by the interface on the remote care provider device, a snapshot of a current heath condition of the patient.

12. The computer-implemented method of claim 1, wherein the writing the data to the computer readable medium in the encrypted format comprises:
encrypting the data;
converting the data to a first set of HL7 embedded portable document format (PDF) message files; and
writing the first set of HL7 embedded portable document format (PDF) message files into the electronic medical record.

13. The computer-implemented method of claim 1, further comprising:
de-registering the remote care provider device to disable communications over a wireless communication channel between the remote care provider device and a secure HIPAA compliant server.

14. A computer system, the computer system comprising:
a memory; and
one or more processors in communications with the memory, wherein the computer system is configured to perform a method, the method comprising:

executing an interface on a remote care provider device, wherein the interface on the remote care provider device is configured to receive and to access data of patients associated with a care provider and to communicate with the patients;
authenticating the remote care provider device based on obtaining an entry in the interface on the remote care provider device;
based on the authenticating, registering the remote care provider device to enable communications over a wireless communication channel between the remote care provider device and a secure HIPAA compliant server;
obtaining, at the secure HIPAA compliant server, from an interface on a mobile device over an Internet connection, data related to a health state of a patient selected from the patients, wherein the secure HIPAA compliant server comprises a processor and a computer readable medium that stores an electronic medical record comprising a medical record number of the patient, historical medical data for the patient associated with the medical record number, and contact information for the care provider for the patient, wherein the contact information is utilized to enable streaming communication between the patient and care provider;
associating, by one or more processors of the secure HIPAA compliant server, a timestamp with the data, associating the data with the medical record number of the patient;
writing, by the processor of the secure HIPAA compliant server, the data to the computer readable medium in an encrypted format;
determining, by the one or more processors, whether the data is in a pre-configured range;
determining, by the one or more processors, based on the contact information that the patient is associated with the care provider;
responsive to determining that the data is not in the pre-configured range and that the patient is associated with the care provider, utilizing the contact information to transmit automatically a real-time alert in the encrypted format over the wireless communication channel to the remote care provider device, wherein the remote care provider device comprises a wireless device associated with the care provider, and wherein, based on determining that the wireless device associated with the care provider is online, the alert is automatically displayed in the interface on the remote care provider device, and wherein based on determining that the wireless device associated with the care provider is not online, the alert is retained at a secured location and displayed in the interface on the remote care provider device when the wireless device associated with the care provider is online, wherein the displaying enables the care provider to utilize the interface on the remote care provider device to access, over the Internet, certain of the data related to the health of the patient and the historical medical data stored on the computer readable medium of the secure HIPAA compliant server, wherein the alert comprises personally identifiable patient data transmitted as an HL7 message file;
responsive to the alert, obtaining a response from the wireless device associated with the care provider of the patient and associating the response with the medical record number of the patient and encrypting and writing the response to the computer readable medium in the encrypted format, wherein the response comprises a medical recommendation based on at least one of: the data, a portion of the historical medical data; and
displaying, on the mobile device, instantaneously upon obtaining, the medical recommendation, based on the streaming communication.

15. The computer system of claim 14, wherein the medical recommendation comprises a diet plan.

16. The computer system of claim 14, the method further comprising:
based on obtaining the medical recommendation, executing a query on a memory resource selected from the group consisting of an external memory resource and an internal memory resource;
responsive to the query, obtaining information describing one or more products compatible with the medical recommendation; and
displaying the information on the mobile device.

17. The computer system of claim 14, wherein the interface on the remote care provider device in which the alert is automatically displayed comprises a dashboard, wherein the dashboard provides the alert and a snapshot of a current heath condition of the patient.

18. The computer system of claim 17, wherein the current health condition of the patient displayed in the dashboard comprises factors at least one factor selected from the group consisting of: socioeconomic information, mental health status, tobacco use, employment status, housing, alcohol use, dietary information, and family support.

19. The computer system of claim 14, wherein the interface on the remote care provider device in which the alert is automatically displayed comprises a notification in a consolidated view of all patients care provider.

20. A computer program product comprising:
a non-transitory computer readable storage medium readable by a processing circuit and storing instructions for execution by the processing circuit for performing a method comprising:
executing an interface on a remote care provider device, wherein the interface on the remote care provider device is configured to receive and to access data of patients associated with a care provider and to communicate with the patients;
authenticating the remote care provider device based on obtaining an entry in the interface on the remote care provider device;
based on the authenticating, registering the remote care provider device to enable communications over a wireless communication channel between the remote care provider device and a secure HIPAA compliant server;
obtaining, at the secure HIPAA compliant server, from an interface on a mobile device over an Internet connection, data related to a health state of a patient selected from the patients, wherein the secure HIPAA compliant server comprises a processor and a computer readable medium that stores an electronic medical record comprising a medical record number of the patient, historical medical data for the patient associated with the medical record number, and contact information for the care provider for the patient, wherein the contact information is utilized to enable streaming communication between the patient and care provider;

associating, by one or more processors of the secure HIPAA compliant server, a timestamp with the data, associating the data with the medical record number of the patient;

writing, by the processor of the secure HIPAA compliant server, the data to the computer readable medium in an encrypted format;

determining, by the one or more processors, whether the data is in a pre-configured range;

determining, by the one or more processors, based on the contact information that the patient is associated with the care provider;

responsive to determining that the data is not in the pre-configured range and that the patient is associated with the care provider, utilizing the contact information to transmit automatically a real-time alert in the encrypted format over the wireless communication channel to the remote care provider device, wherein the remote care provider device comprises a wireless device associated with the care provider, and wherein, based on determining that the wireless device associated with the care provider is online, the alert is automatically displayed in the interface on the remote care provider device, and wherein based on determining that the wireless device associated with the care provider is not online, the alert is retained at a secured location and displayed in the interface on the remote care provider device when the wireless device associated with the care provider is online, wherein the displaying enables the care provider to utilize the interface on the remote care provider device to access, over the Internet, certain of the data related to the health of the patient and the historical medical data stored on the computer readable medium of the secure HIPAA compliant server, wherein the alert comprises personally identifiable patient data transmitted as an HL7 message file;

responsive to the alert, obtaining a response from the wireless device associated with the care provider of the patient and associating the response with the medical record number of the patient and encrypting and writing the response to the computer readable medium in the encrypted format, wherein the response comprises a medical recommendation based on at least one of: the data, a portion of the historical medical data; and displaying, on the mobile device, instantaneously upon obtaining, the medical recommendation, based on the streaming communication.

* * * * *